(12) United States Patent
Jun et al.

(10) Patent No.: US 11,440,941 B2
(45) Date of Patent: Sep. 13, 2022

(54) CANCER-TREATING RECOMBINANT PROTEIN THAT IMPROVES THE ACTIVITY OF CYTOTOXIC KILLER CELLS TARGETING CANCER CELLS AND USE THEREOF

(71) Applicant: GWANGJU INSTITUTE OF SCIENCE AND TECHNOLOGY, Gwangju (KR)

(72) Inventors: Chang-Duk Jun, Gwangju (KR); Bu Nam Jeon, Gwangju (KR); Hey-Ran Kim, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 218 days.

(21) Appl. No.: 16/112,826

(22) Filed: Aug. 27, 2018

(65) Prior Publication Data

US 2019/0309036 A1 Oct. 10, 2019

(30) Foreign Application Priority Data

Apr. 10, 2018 (KR) .................. 10-2018-0041625

(51) Int. Cl.
| | | |
|---|---|---|
| *C07K 14/47* | (2006.01) | |
| *A61P 35/00* | (2006.01) | |
| *A61K 35/17* | (2015.01) | |
| *C12N 5/0783* | (2010.01) | |
| *A61K 38/17* | (2006.01) | |

(52) U.S. Cl.
CPC .......... *C07K 14/4716* (2013.01); *A61K 35/17* (2013.01); *A61K 38/17* (2013.01); *A61P 35/00* (2018.01); *C12N 5/0638* (2013.01); *C07K 2319/10* (2013.01)

(58) Field of Classification Search
CPC .... A61K 35/17; C12N 5/0636; C12N 5/0637; C12N 5/0638; C12N 5/0639
See application file for complete search history.

(56) References Cited

U.S. PATENT DOCUMENTS

| | | | | |
|---|---|---|---|---|
| 5,674,980 A | * | 10/1997 | Frankel ................ | A61K 47/62 530/350 |
| 2004/0053233 A1 | * | 3/2004 | Lorens ................ | C12Q 1/6883 435/6.14 |

FOREIGN PATENT DOCUMENTS

AU        2013203190 B2        5/2013

OTHER PUBLICATIONS

Na and Jun (BMB Reports 2015; 48(7): 369-370), (Year: 2015).*
Jo et al. (J Leukocyte Biology May 11, 2018) (Year: 2018).*
Schwarze et al. (Science Sep. 3, 1999, 285: 1569-1572), (Year: 1999).*
Chang-Duk Jun, "Development and Application of Novel Peptides That Control Novel Protein TAGLN2 in Immunological Synapse", Gwangju Institute of Science and Technology, Jun. 18, 2012, 29 pages.
Radvanyi, Laszlo G., et al. "CD28 costimulation inhibits TCR-induced apoptosis during a primary T cell response." The Journal of Immunology 156.5 (1996): 1788-1798.
Samstag, Yvonne, et al. "Actin cytoskeletal dynamics in T lymphocyte activation and migration." Journal of leukocyte biology 73.1 (2093): 30-48.
Na, Bo-Ra, et al. "TAGLN2 regulates T cell activation by stabilizing the actin cytoskeleton at the immunological synapse." J Cell Biol 209.1 (2015): 143-162.
UniProtKB—P37802 (TAGL2_HUMAN), Jan. 23, 2007, 12 pages
Bu-Nam Jeon et al., "Actin stabilizer TAGLN2 potentiates adoptive T cell therapy by boosting the inside-out costimulation via lymphocyte function-associated atigen-1", Oncoimmunology, published Sep. 6, 2018, vol. 7, No. 12, 19 pages.
Ming-Zhi Han et al., "TAGLN2 is a candidate prognostic biomarker promoting tumorigenesis in human gliomas", Journal of Experimental & Clinical Cancer Research, published Nov. 6, 2017, 36:155, 14 pages.

* cited by examiner

*Primary Examiner* — Peter J Reddig
(74) *Attorney, Agent, or Firm* — Brooks Kushman P.C.

(57) ABSTRACT

A cancer killer cell in which a therapeutic recombinant protein or recombinant protein which improves cytotoxic activity of the cancer killer cell is loaded. In addition, a pharmaceutical composition including the recombinant protein or a recombinant protein-loaded cancer killer cell is disclosed. Further, disclosed is a method for preparing a recombinant protein-loaded cancer killer cell.

13 Claims, 9 Drawing Sheets

Specification includes a Sequence Listing.

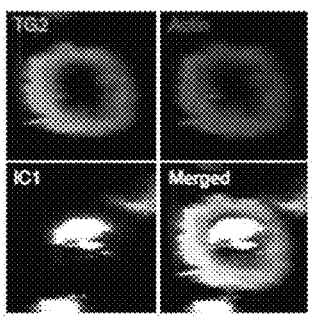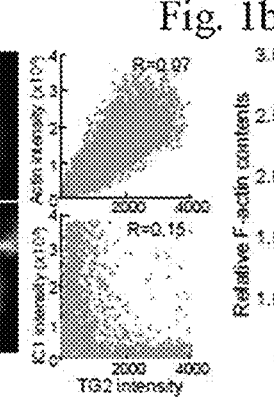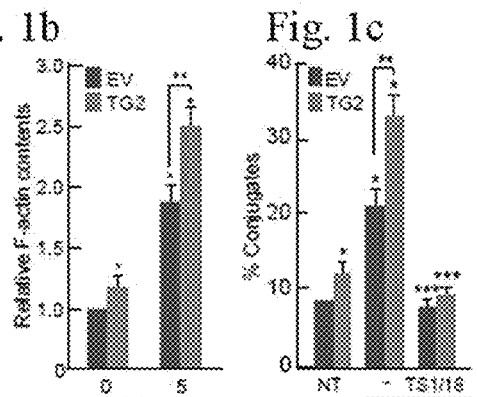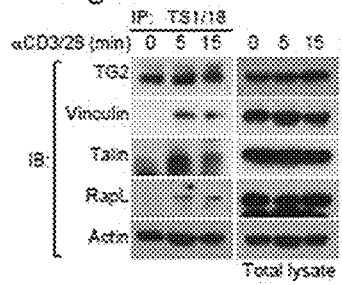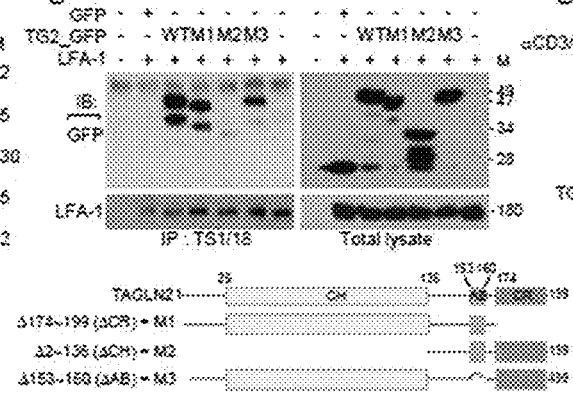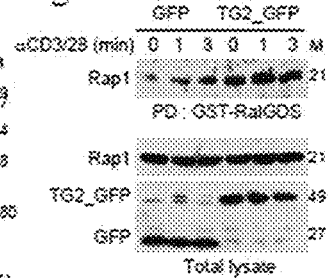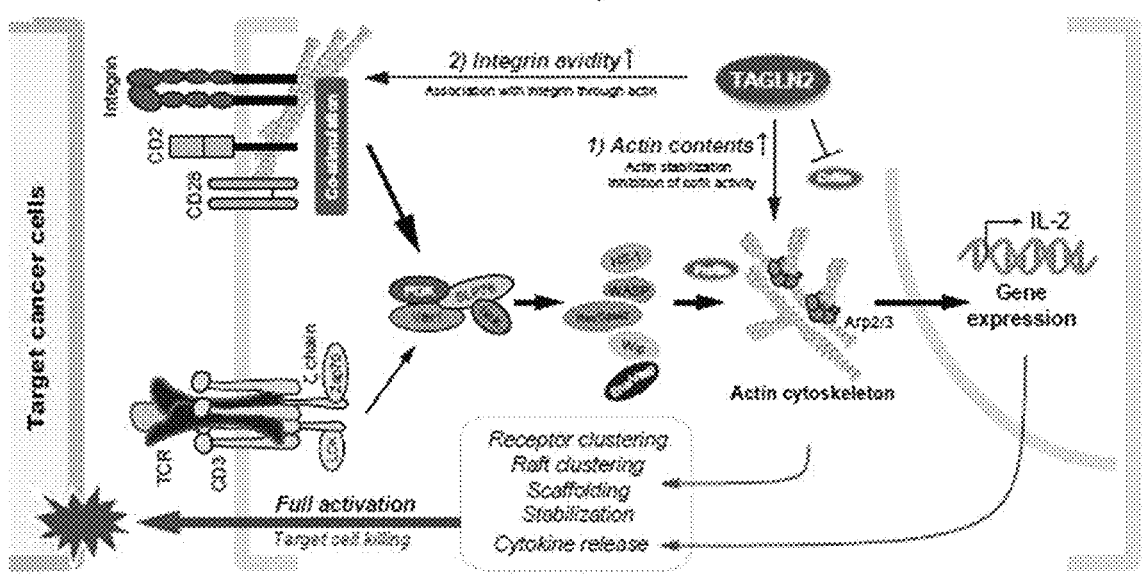

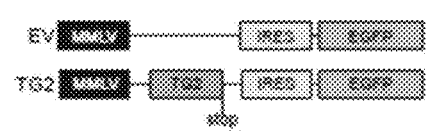
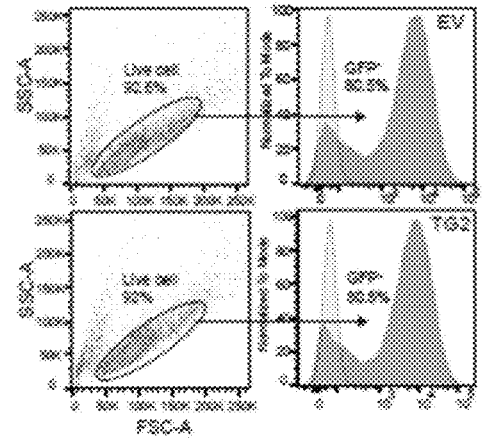
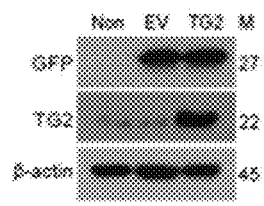
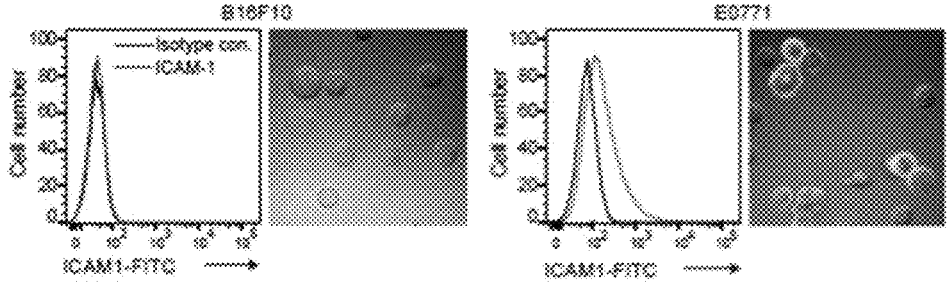
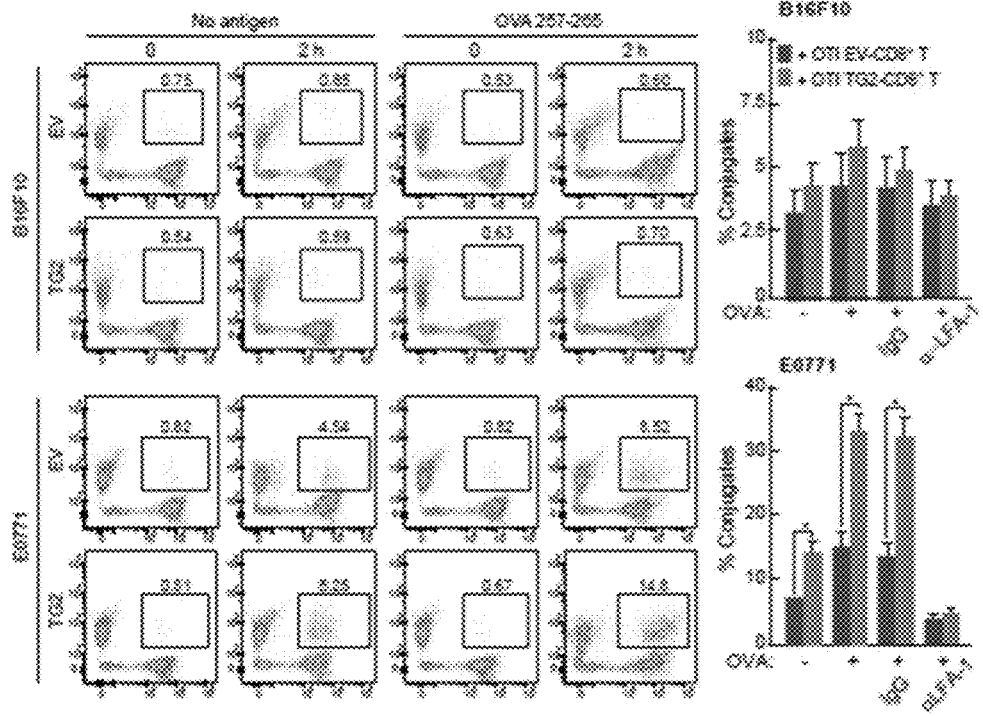

Fig. 4a
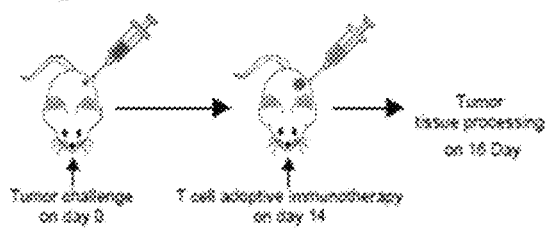
Fig. 4b
Fig. 4c
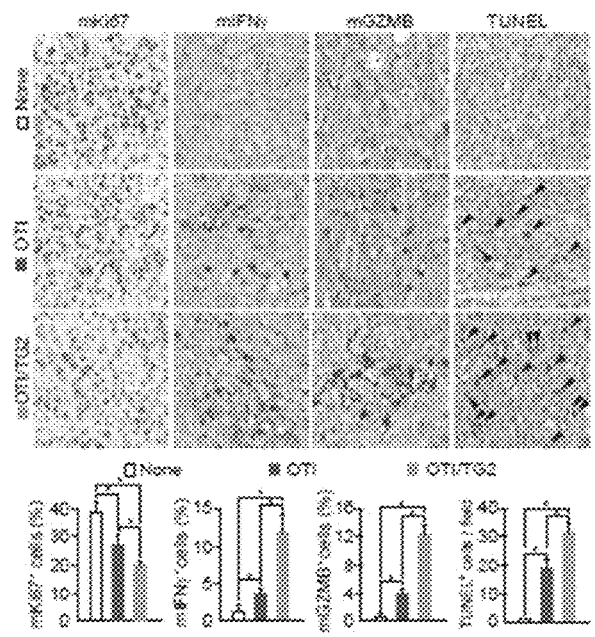
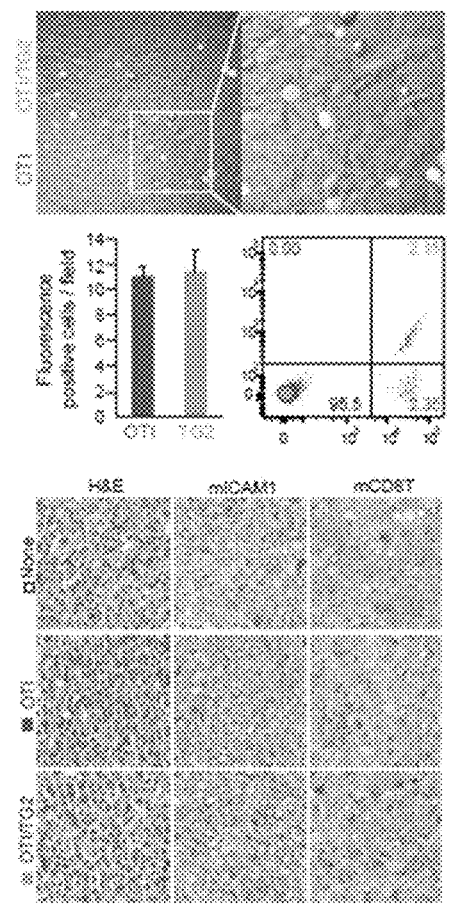
Fig. 4d
Fig. 4e
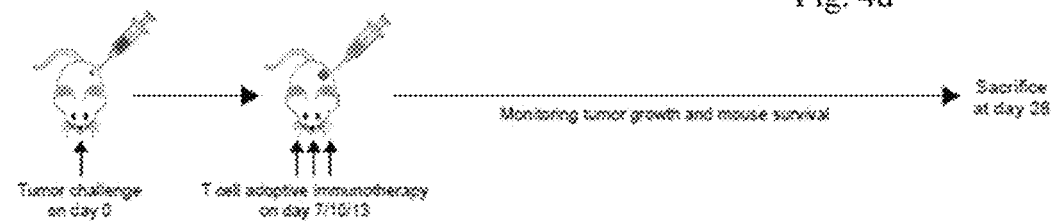
Fig. 4f 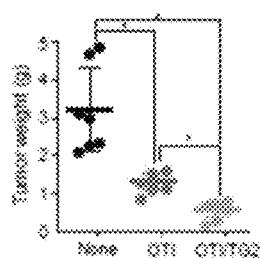 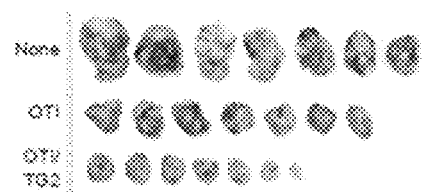 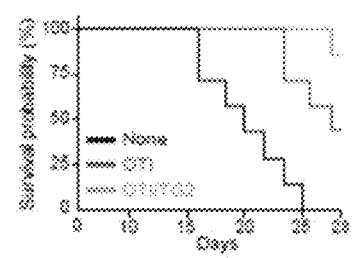
Fig. 4g  Fig. 4h

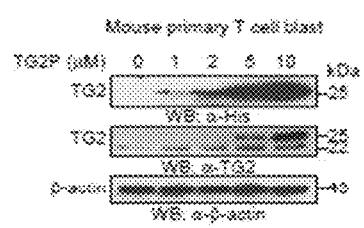
Fig. 5a
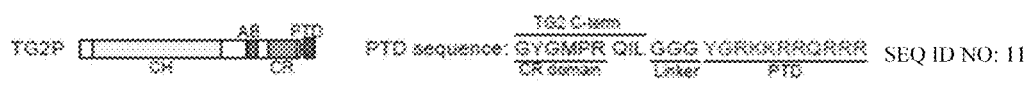
Fig. 5b
Fig. 5c
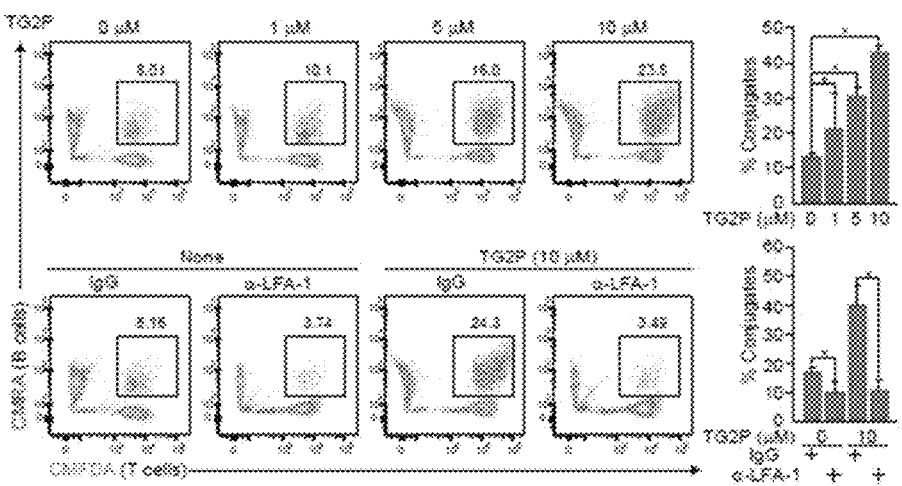
Fig. 5d
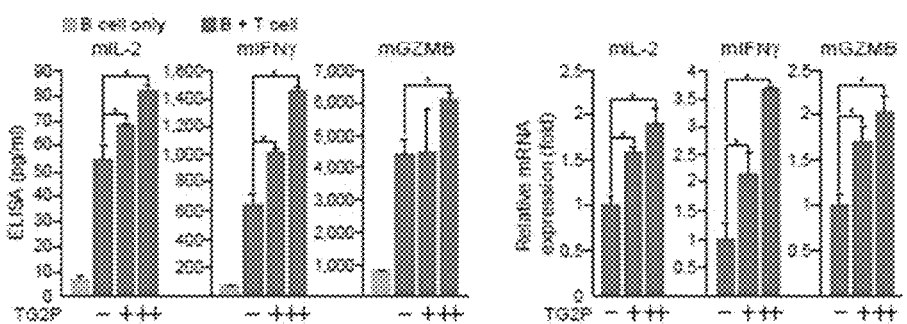
Fig. 5e

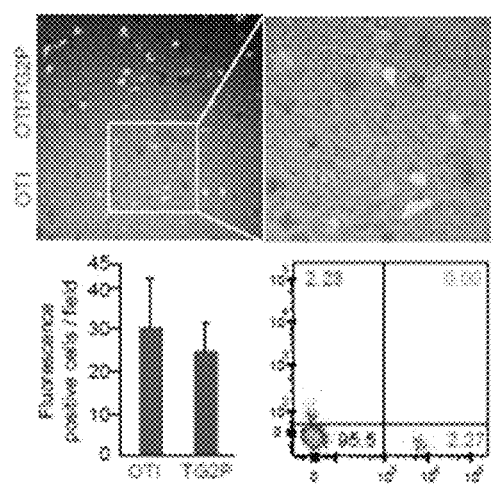
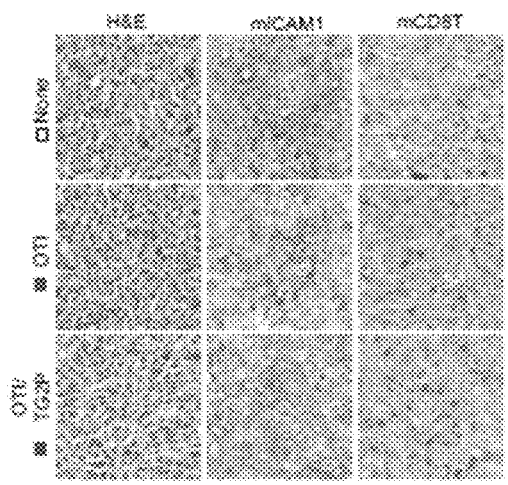
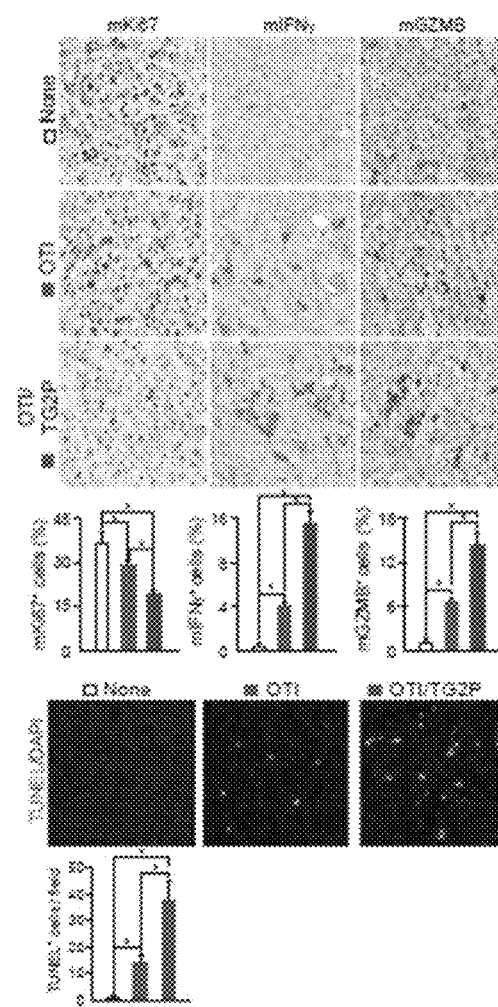
Fig. 7a
Fig. 7b
Fig. 7c
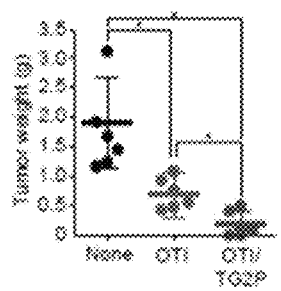
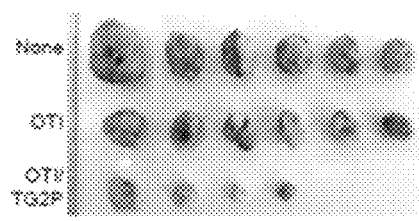
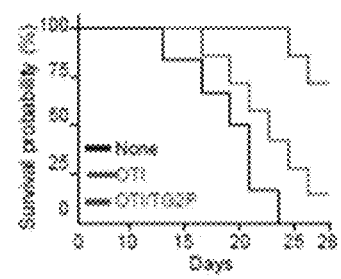
Fig. 7d
Fig. 7e
Fig. 7f

SEQUENCE LISTING

<160> NUMBER OF SEQ ID NOS: 11

<210> SEQ ID NO 1
<211> LENGTH: 199
<212> TYPE: PRT
<213> ORGANISM: Unknown
<220> FEATURE:
<223> OTHER INFORMATION: TAGLN2

<400> SEQUENCE: 1

```
Met Ala Asn Arg Gly Pro Ala Tyr Gly Leu Ser Arg Glu Val Gln Gln
1               5                   10                  15

Lys Ile Glu Lys Gln Tyr Asp Ala Asp Leu Glu Gln Ile Leu Ile Gln
            20                  25                  30

Trp Ile Thr Thr Gln Cys Arg Lys Asp Val Gly Arg Pro Gln Pro Gly
        35                  40                  45

Arg Glu Asn Phe Gln Asn Trp Leu Lys Asp Gly Thr Val Leu Cys Glu
    50                  55                  60

Leu Ile Asn Ala Leu Tyr Pro Glu Gly Gln Ala Pro Val Lys Lys Ile
65                  70                  75                  80

Gln Ala Ser Thr Met Ala Phe Lys Gln Met Glu Gln Ile Ser Gln Phe
                85                  90                  95

Leu Gln Ala Ala Glu Arg Tyr Gly Ile Asn Thr Thr Asp Ile Phe Gln
            100                 105                 110

Thr Val Asp Leu Trp Glu Gly Lys Asn Met Ala Cys Val Gln Arg Thr
        115                 120                 125

Leu Met Asn Leu Gly Gly Leu Ala Val Ala Arg Asp Asp Gly Leu Phe
    130                 135                 140

Ser Gly Asp Pro Asn Trp Phe Pro Lys Lys Ser Lys Glu Asn Pro Arg
145                 150                 155                 160

Asn Phe Ser Asp Asn Gln Leu Gln Glu Gly Lys Asn Val Ile Gly Leu
                165                 170                 175

Gln Met Gly Thr Asn Arg Gly Ala Ser Gln Ala Gly Met Thr Gly Tyr
            180                 185                 190

Gly Met Pro Arg Gln Ile Leu
        195
```

<210> SEQ ID NO 2
<211> LENGTH: 11
<212> TYPE: PRT
<213> ORGANISM: Unknown
<220> FEATURE:
<223> OTHER INFORMATION: PTD

<400> SEQUENCE: 2

```
Tyr Gly Arg Lys Lys Arg Arg Gln Arg Arg Arg
1               5                   10
```

<210> SEQ ID NO 3
<211> LENGTH: 19
<212> TYPE: DNA
<213> ORGANISM: Artificial Sequence
<220> FEATURE:
<223> OTHER INFORMATION: IL-2 (Forward)

<400> SEQUENCE: 3
cacgtcttgc acttgtcac                    19

<210> SEQ ID NO 4
<211> LENGTH: 21

```
<212> TYPE: DNA
<213> ORGANISM: Artificial Sequence
<220> FEATURE:
<223> OTHER INFORMATION: IL-2 (Reverse)

<400> SEQUENCE: 4
ccttcttggg catgtaaaac t                                       21

<210> SEQ ID NO 5
<211> LENGTH: 20
<212> TYPE: DNA
<213> ORGANISM: Artificial Sequence
<220> FEATURE:
<223> OTHER INFORMATION: INFgamma (Forward)

<400> SEQUENCE: 5
gctctgagac aatgaacgct                                         20

<210> SEQ ID NO 6
<211> LENGTH: 20
<212> TYPE: DNA
<213> ORGANISM: Artificial Sequence
<220> FEATURE:
<223> OTHER INFORMATION: INFgamma (Reverse)

<400> SEQUENCE: 6
aaagagataa tctggctctg                                         20

<210> SEQ ID NO 7
<211> LENGTH: 22
<212> TYPE: DNA
<213> ORGANISM: Artificial Sequence
<220> FEATURE:
<223> OTHER INFORMATION: GZMB (Forward)

<400> SEQUENCE: 7
tttcatcctg taattggact aa                                      22

<210> SEQ ID NO 8
<211> LENGTH: 18
<212> TYPE: DNA
<213> ORGANISM: Artificial Sequence
<220> FEATURE:
<223> OTHER INFORMATION: GZMB (Reverse)

<400> SEQUENCE: 8
gcgatctcca cacttctc                                           18

<210> SEQ ID NO 9
<211> LENGTH: 20
<212> TYPE: DNA
<213> ORGANISM: Artificial Sequence
<220> FEATURE:
<223> OTHER INFORMATION: GAPDH (Forward)

<400> SEQUENCE: 9
gcacagtcaa ggccgagaat                                         20

<210> SEQ ID NO 10
<211> LENGTH: 20
<212> TYPE: DNA
<213> ORGANISM: Artificial Sequence
<220> FEATURE:
<223> OTHER INFORMATION: GAPDH (Reverse)

<400> SEQUENCE: 10
```

```
gccttctcca tggtggtgaa                                              20

<210> SEQ ID NO 11
<211> LENGTH: 23
<212> TYPE: PRT
<213> ORGANISM: Artificial Sequence
<220> FEATURE:
<223> OTHER INFORMATION: TG2P fused with PTD

<400> SEQUENCE: 11

Gly Tyr Gly Met Pro Arg Gln Ile Leu Gly Gly Gly Tyr Gly Arg Lys
1               5                   10                  15

Lys Arg Arg Gln Arg Arg Arg
            20
```

CANCER-TREATING RECOMBINANT PROTEIN THAT IMPROVES THE ACTIVITY OF CYTOTOXIC KILLER CELLS TARGETING CANCER CELLS AND USE THEREOF

CROSS-REFERENCE TO RELATED APPLICATIONS

This application filed on, which claims priority to Patent Application No. KR 10-2018-0041625 Apr. 10, 2018.

SEQUENCE LISTING

The text file Sequence_listing_OPA18294_ST25 of 4 KB created Sep. 30, 2020, filed herewith, is hereby incorporated by reference.

Technical Field

The present disclosure relates to a cancer killer cell in which a therapeutic recombinant protein or recombinant protein which improves cytotoxic activity of the cancer killer cell is loaded. In addition, the present disclosure relates to a pharmaceutical composition comprising the recombinant protein or a recombinant protein-loaded cancer killer cell. Further, the present disclosure relates to a method for preparing a recombinant protein-loaded cancer killer cell.

BACKGROUND

Cancer immunotherapy has led to important clinical developments and provided new methods for cancer management. One new approach to cancer immunotherapy is to target an immune checkpoint protein such as programmed death-1 (PD-1) or cytotoxic T lymphocyte antigen 4 (CTLA 4; cytotoxic T lymphocyte antigen 4) in order to reactivate tumor-infiltrated lymphocytes (TILs); however, this has a disadvantage of low reaction efficiency.

Another way to approach cancer immunotherapy is to use T cells or natural killer (NK) cells including a chimeric antigen receptor (CAR) as a "cancer hunter cell", but this has a disadvantage in that due to a strong immunosuppressive tumor microenvironment that can be protected from immune attack, the cell cannot be used for solid cancer. In this regard, many studies have been conducted to develop new strategies to enhance the anti-tumor activity of the reactivated TIL- or CAR-loaded T cells and NK cells.

The immunological synapse (IS) refers to a multi-molecule functional structure formed at the interface between a T cell and an antigen-presenting cell (APC) expressing an appropriate peptide/MHC complex. Stimulation of TCR, which is a primary cellular signal of T cells, is known to result in actin polymerization at the outermost distal-SMAC (d-SMAC). The absence of costimulation, which is a secondary signal, is known to make causing complete T cell activation impossible, as sufficient large-scale actin polymerization does not occur in d-SMAC (Radvanyi, L. G. et al. *Journal of immunology* 156, 1788-1798 (1996), Samstag, Y. et al., *Journal of leukocyte biology* 73, 30-48 (2003)). Interestingly, solid tumors have a microenvironment in which secondary costimulation is suppressed, and thus have a problem in that tumor cytotoxic activity is not adequately expressed even if cytotoxic T cells penetrate a tumor site. Accordingly, controlling actin polymerization of cytotoxic T cells in an immunological synapse has suggested a new method which facilitates overcoming an immunosuppressive environment and insufficient costimulation signals in a tumor microenvironment. In this regard, the present inventors were to overcome the limitations of immunotherapy and CAR-T and NK cell treatment, which apply suppression of immune checkpoints by controlling actin polymerization in an immunological synapse.

Under such circumstances, the present inventors endeavored to develop a technique of controlling actin polymerization in an immunological synapse, and as a result, found that TAGLN2, a comparatively small 22 kDa actin-binding protein, can stabilize actin polymerized in an immunological synapse by TCR stimulation, and prepared a recombinant vector for overexpression of TAGLN2 in a T cell or a retrovirus vector facilitating stable expression of TAGLN2. They also found that the cytotoxic T cells into which the TAGLN2 recombinant protein or retrovirus containing genetic codes of the TAGLN2 is introduced has excellent adhesion activity and proved the effect of the cytotoxic T cells on pronounced reduction of tumor growth in a mouse model with a solid cancer, thereby completing the present disclosure.

DISCLOSURE

Technical Problem

An object of the present disclosure is to provide a recombinant protein for treating cancer consisting of an amino acid sequence of SEQ ID NO: 1, which is loaded in a cancer killer cell to improve cytotoxic activity of the cancer killer cell.

Another object of the present disclosure is to provide a recombinant protein-loaded cancer killer cell which includes the recombinant protein above.

Another object of the present disclosure is to provide a pharmaceutical composition for treating cancer, comprising i) a recombinant protein for treating cancer consisting of an amino acid sequence of SEQ ID NO: 1, which is loaded in a cancer killer cell to improve cytotoxic activity of the cancer killer cell; ii) a recombinant protein, wherein a PTD is further fused into the i) protein; or iii) a cancer killer cell in which the recombinant protein is loaded.

Another object of the present disclosure is to provide a method for treating cancer, comprising administering the composition above in a pharmaceutically effective amount to a subject suspected of having a cancer excluding humans.

Another object of the present disclosure is to provide a method for producing a recombinant protein-loaded cancer killer cell, comprising (a) fusing a PTD into an amino acid of SEQ ID NO: 1; and (b) introducing the fusion protein of (a) into a cancer killer cell.

Another object of the present disclosure is to provide a method for producing a recombinant protein-loaded cancer killer cell, comprising: transducing into a cancer killer cell using retrovirus comprising a polynucleotide encoding an amino acid sequence of SEQ ID NO: 1.

SUMMARY

Technical Solution

An aspect of the present disclosure is to provide a recombinant protein for treating cancer consisting of an amino acid sequence of SEQ ID NO: 1, which is loaded in a cancer killer cell to improve cytotoxic activity of the cancer killer cell.

In addition, the recombinant protein may further be fused with a protein transduction domain (PTD); specifically, the fusion of PTD is by a peptide linker or direct fusion.

Nucleotide sequences of the protein of SEQ ID NO: 1, and the PTD protein and a specific nucleotide sequence of a gene encoding the same can be obtained from a known database such as NCBI GenBank.

Any recombinant protein of the present disclosure, which can stabilize actin polymerized in an immunological synapse by T cell antigen receptor signaling or has activity of increasing adhesion of cytotoxic T cells onto cancer cells by the interaction between the LFA-1 of the recombinant protein-loaded cancer killer cell and ICAM-1 of target cell, can be included within the scope of the present disclosure as long as it has the above known sequence or a sequence having a homology thereto of 80% or higher, specifically 85% or higher, more specifically 90% or higher, and even more specifically 95% or higher.

As used herein, the term "cancer killer cell" may refer to a tumor-infiltrated T lymphocyte (TIL) or T cell or natural killer (NK) cell or including chimeric antigen receptor (CAR), but is not limited thereto.

As used herein, the term "homology" refers to the degree of similarity of to an amino acid sequence of a wild-type protein or nucleotide sequence encoding the same, and includes a sequence having said or higher sequence homology to the amino acid sequence or nucleotide sequence of the present disclosure. The homology may be determined by comparison with the naked eye, but also using a bioinformatic algorithm which provides analysis results of a degree of homology of target sequences by aligning them in parallel for comparison. The homology between the two amino acid sequences may be indicated as percentages. Useful automated algorithms may be used in GAP, BESTFIT, FASTA, and TFASTA computer software modules of the Wisconsin Genetics Software Package (Genetics Computer Group, Madison, Wis., USA). The alignment algorithms automated in these modules include the Needleman & Wunsch, the Pearson & Lipman, and the Smith & Waterman sequence alignment algorithms. Other useful algorithms and homology determinations on alignment are already automated in software such as FASTP, BLAST, BLAST2, PSIBLAST, and CLUSTAL W.

Meanwhile, as used herein, "protein including a particular SEQ ID NO", as long as it has activity identical or corresponding to a protein including the same SEQ ID NO, may not exclude an insignificant addition of a sequence before or after the amino acid sequence, a naturally occurring mutation thereof. In the case of proteins having such sequence addition or mutation, it is apparent that they are also included within the scope of the present disclosure.

As used herein, the term "TAGLN2" or "transgelin-2" refers to a protein encoded by a TAGLN2 gene in humans, and the function of the protein has not been clearly known.

Specifically, transgelin (TAGLN), a 22 kDa actin-binding protein, was first discovered in chicken gizzard smooth muscle, and has been called "transgelin" due to its transformation sensitive and rapid actin-gelling properties. Among three TAGLNs that have 80% homology, TAGLN2 are predominantly expressed in T cells and stabilize cortical F-actin to maintain immunological synapse (IS). Additionally, the overexpression of TAGLN2 causes LFA-1 activation after stimulating TCR, and such biochemical characteristics make the TAGLN2 advantageous when applied to cancer immunotherapy.

TAGLN2, for the purpose of the present disclosure, activates LFA-1 by "inside-out" signaling, and thus can minimize effects on non-targets, which may arise and be disadvantageous when artificially activating LFA-1 only. Further, the activation of the signal transduction pathway increases the production of IL-2 that is essential for extended survival of T cells, and the formation of stable ISs between cytotoxic T cells or NK cells and tumor target cells increases cytotoxicity to the tumor, thereby facilitating an effective application to the cancer treatment.

The term "TAGLN2" can be interchangeably used with "transgelin-2" and "TG2", and specifically refers to amino acids of SEQ ID NO: 1. The genetic information of the protein can be obtained from a known database; for example, National Center for Biotechnology Information (NCBI) GenBank, etc., but is not limited thereto.

As used herein, the term "protein transduction domain (PTD)" refers to a small protein domain and is used to deliver particular therapeutic macromolecules into a eukaryotic cell. The PTD in the present disclosure is used to overcome the disadvantages of the virus-mediated gene transfer system that has inconsecutive transduction efficiency, long preparation time, high costs, and safety issues. The genetic information of the PTD can be obtained from a known database; for example, National Center for Biotechnology Information (NCBI) GenBank, etc., but is not limited thereto. A particular PTD, specifically consisting of amino acids of SEQ ID NO: 2, may be used in the present disclosure to deliver the TAGLN2 into cells, but is not limited thereto.

The recombinant protein of the present disclosure may stabilize actin polymerized in an immunological synapse by T cell antigen receptor signaling, but is not limited thereto.

In the present disclosure, the recombinant protein loaded in a cancer killer cell may show increased cytokine expression compared to a control group having no recombinant protein loaded, but is not limited thereto.

It was confirmed in the Examples of the present disclosure that when a TAGLN-transduced T cell is adhered to a cancer cell line, excellent cytokine release and cytotoxicity were exhibited compared to the control group (Example 3 and FIG. 3). The cytokine may be at least one of mIL-2, mIFNγ, and mGZMB, but is not limited thereto.

Further, in vivo tumor growth in mice was examined, and as a result, it was shown that mice in which TAGLN2-transduced T cells were injected showed significantly excellent survivability compared to untreated mice and mice in which T cells having no transduced TAGLN2 were introduced (FIG. 4).

Based on such results, the present inventors found that the recombinant protein for treating cancer consisting of an amino acid sequence of SEQ ID NO: 1, which is loaded in a cancer killer cell to improve cytotoxic activity of the cancer killer cell, enhances the adhesion activity as well as cytokine release activity and cytotoxicity of the killer cells, and has excellent survivability by anticancer effects, thereby confirming the cancer treatment effect of the recombinant protein when loaded into a cancer killer cell. They further confirmed that the recombinant protein can be applied to cancer treatment that has overcome the disadvantages of the existing virus-mediated gene transfer system, i.e., inconsecutive transduction efficiency, long preparation time, high costs, and safety issues.

Another aspect of the present disclosure is to provide a recombinant protein-loaded cancer killer cell, wherein the cancer killer cell comprises the recombinant protein above.

The loading of the recombinant protein into the cancer killer cell may be performed by i) introducing the PTD into the recombinant protein for treating cancer consisting of an amino acid sequence of SEQ ID NO: 1, which is loaded in a cancer killer cell to improve cytotoxic activity of the cancer killer cell in the form of a fused recombinant protein, or ii) transducing a polynucleotide encoding a recombinant protein for cancer treatment consisting of an amino acid sequence of SEQ ID NO: 1 using a retrovirus, but is not limited thereto.

Another aspect of the present disclosure is to provide a pharmaceutical composition for treating cancer, comprising i) a recombinant protein for treating cancer consisting of an amino acid sequence of SEQ ID NO: 1, which is loaded in a cancer killer cell to improve cytotoxic activity of the cancer killer cell; ii) a recombinant protein, wherein a PTD is further fused into the i) protein; or iii) a cancer killer cell in which the recombinant protein is loaded.

For the purpose of the present disclosure, the pharmaceutical composition for treating cancer can show a cancer treatment effect by stabilizing actin polymerized in an immunological synapse by stimulation of a T-cell antigen receptor. Additionally, the recombinant protein, when loaded in a cancer killer cell, shows increased cytokine expression compared to the control group having no recombinant protein loaded, leading to the cancer treatment effect.

As used herein, the term "cancer" refers to a tumor caused by the abnormal growth of body tissue or a disease that forms a tumor. In particular, the cancer is caused by loss and lack of cytotoxic activity of immune cells, etc., and thus can be treated by controlling cell death. In the present disclosure, the terms "cancer" and "tumor" can interchangeably be used.

Specifically, the cancer is not limited as long as its symptoms can be ameliorated, mitigated, alleviated, or treated by the recombinant protein of the present invention or T cells into which the protein is introduced. As specific examples, the cancer may be gastric cancer, colon cancer, breast cancer, lung cancer, non-small-cell lung cancer, bone cancer, pancreatic cancer, skin cancer, head cancer, head and neck cancer, melanoma, uterine cancer, ovarian cancer, colon cancer, small intestine cancer, rectal cancer, anal cancer, fallopian tube cancer, endometrial cancer, cervical cancer, vaginal cancer, vulva cancer, Hodgkin's disease, esophageal cancer, lymph node cancer, bladder cancer, gall bladder cancer, endocrine cancer, prostate cancer, adrenal gland cancer, soft tissue sarcoma, urethral cancer, penile cancer, chronic or acute leukemia, lymphocytic lymphoma, renal cancer, ureteral cancer, renal pelvic cancer, central nervous system (CNS) tumor, spinal cord tumor, brainstem glioma, or pituitary adenoma; and more specifically may be breast cancer, but is not limited thereto. Further, the cancer may be a cancer expressing ICAM-1, but is not limited thereto.

As described above, the cancer killer cells in which the recombinant protein of the present invention is loaded are strongly attached to cancer cells, thereby having an effect of inducing growth suppression and death of the cancer cells. As long as it can be treated by inducing growth suppression and death of the cancer cells, the cancer is not limited to a particular type of cancer, and can be treated by the pharmaceutical composition of the present invention.

The Examples of the present invention revealed the effects of growth suppression and death of the cancer cells induced by the recombinant protein of the present invention or the recombinant protein-loaded cancer killer cells representatively using breast cancer cells.

As used herein, the term "treatment" refers to any behavior that improves or ameliorates symptoms of cancer by administering a composition containing the recombinant protein or a cancer killer cell in which the recombinant protein is loaded.

The pharmaceutical composition of the present invention can be used as a single agent or in combination with an additional drug known to have a therapeutic effect on cancer. By formulating using a pharmaceutically acceptable carrier or excipient, the pharmaceutical composition can be prepared in a unit dose form or encapsulated into a multi-dose container.

Further, the pharmaceutical composition of the present invention may be lyophilized, or if necessary, another conventional additive such as an antioxidant, a buffer solution, and/or a bacteriostatic agent may be added. By additionally adding a diluting agent, dispersing agent, surfactant, binding agent, lubricant, etc., the pharmaceutical composition can be formulated into an injectable formulation such as an aqueous solution, suspension, emulsion, etc., a pill, a capsule, a granule, a tablet, etc.

For the purpose of the present invention, however, it is preferable that a therapeutically effective amount specifically for a particular patient depends upon various factors including the type and extent of a target response, specific compositions according to whether other agents are used therewith or not, the patient's age, body weight, health condition, gender, diet, the time and route of administration, the secretion rate of the composition, the duration of treatment, and other drugs used in combination or simultaneously with the composition, as well as other similar factors well known in the medical field.

The pharmaceutical composition of the present invention must be loaded into a cytotoxic cell to be administered, but may be administered in combination with other therapeutic agents and administered sequentially or simultaneously with conventional therapeutic agents. The pharmaceutical composition may be administered in a single- or multiple-dosage form. It is important to administer the pharmaceutical composition in a minimum amount that can exhibit a maximal effect without causing any side effects, and the amount can be easily determined by one of ordinary skill in the art.

As used herein, the term "administration" refers to the introduction of a particular substance into a subject by an appropriate method. It can be any effective and convenient routes of administration including, for example, intravenous administration.

The pharmaceutical composition according to the present invention must be loaded in a cytotoxic cell and administered via the pathway of immune cell therapy by a method conventionally used in the technical field. The frequency of administration of the composition according to the present invention is not particularly limited.

Another aspect of the present invention is to provide a method for treating cancer comprising administering the composition to a subject suspected of having a cancer excluding humans in a pharmaceutically effective amount.

As used herein, the term "subject" may refer to all animals including humans in which a cancer has been developed or is likely to be developed. The animal may not only include a human but may also include a mammal such as a cow, horse, sheep, pig, goat, camel, antelope, dog, cat, etc., but is not limited thereto.

Specifically, the treatment method of the present invention may comprise administering the composition to a subject suspected of having a cancer excluding humans in a pharmaceutically effective amount.

Another aspect of the present invention is to provide method for producing a recombinant protein-loaded cancer killer cell, comprising (a) fusing a PTD into an amino acid of SEQ ID NO: 1; and (b) introducing the fusion protein of (a) into a cancer killer cell.

To prepare a recombinant protein (TG2P) which is transduced into T cells more easily and faster for the purpose of the present invention, a PTD was fused with TAGLN2, and TAGLN recombinant protein (SEQ ID NO: 1) was prepared.

In the Examples of the present invention, a TAGLN2 recombinant protein (TG2P) fused with PTD was prepared (FIG. 5a), and the prepared TG2P was easily internalized into T cells that stayed stable for at least 24 hours (FIGS. 5b and 5c). The cancer killer cell into which the TG2P was transduced was shown to have the tumor suppression effect.

Based on the above, TG2P was confirmed to be easily transduced into cytotoxic T cells and be applicable to cancer treatment similarly to the case where TG2P in which PTD is introduced into TAGLN2 introduces TAGLN2 in a T cell using a virus as a mediator.

Another aspect of the present invention is to provide a method for producing a recombinant protein-loaded cancer killer cell, comprising: transducing into a cancer killer cell using retrovirus comprising a polynucleotide encoding an amino acid sequence of SEQ ID NO: 1.

It was measured in the Examples of the present invention whether cytotoxic T cells has enhanced activity of adhesion onto cancer cells through retroviral transduction including a polynucleotide encoding TAGLN2, and as a result, the T cells showed excellent adhesion onto a cancer cell line which has increased ICAM-1 expression (Example 2).

Advantageous Effects

The recombinant protein for treating cancer of the present invention or the recombinant protein-loaded cancer killer cells, by increasing adhesion activity thereof, can suppress the cancer cell growth. Accordingly, a pharmaceutical composition including the same can be used in the cancer treatment.

BRIEF DESCRIPTION OF DRAWINGS

FIG. 1a-FIG. 1g shows that TAGLN2 physically interacted with LFA-1 and increased Rap1 activity. FIG. 1a shows localization of TAGLN2 (TG2), F-actin, and ICAM-1 (IC1) at the interface between T and B cells. Jurkat T cells expressing TG2_GFP and LifeA_mRFP (red) were conjugated with SEB-loaded Raji B cells stained with IC1_Cy5 (white) for 30 minutes. Three-dimensional reconstruction revealed the en face positions of contact interface areas between cells. Colocalization of TG2 and LifeA or TG2 and IC1 signals was determined by Pearson's correlation coefficient (R). FIG. 1b Jurkat T cells expressing GFP and TG2_GFP were stimulated with anti-CD3/28 for 5 minutes. F-actin content was quantified using flow cytometry. Data is presented as relative fluorescence intensity compared with that in Jurkat T cells expressing GFP at 0 minutes. FIG. 1c shows conjugate formation between Jurkat T cells expressing GFP or TG2_GFP cells and SEB-loaded Raji B cells. FIG. 1d Jurkat T cells were stimulated with anti-CD3/28 for the indicated times. Samples were immunoprecipitated with TS1/18 (anti-LFA-1 antibodies) and blotted with antibodies against the indicated proteins. FIG. 1e HEK293T cells were cotransfected with LFA-1 and different mutants of TG2, and immunoprecipitation and Western blotting were performed. The schematic diagram shows the deletion mutants of TAGLN2 (M1, M2, and M3). FIG. 1f shows activity of Rap1. Jurkat T cells expressing GFP and TG2_GFP were stimulated with anti-CD3/28 antibodies, and pull-down assays were performed. GTP-bound Rap1 was visualized by immunoblotting using anti-Rap1 antibodies. Data is representative of three independent experiments (b-f). *P<0.05.

FIG. 1g shows a schematic cartoon representing the potential mechanisms of TAGLN2 in T cells.

FIG. 2a-FIG. 2e shows that retroviral transduction of TAGLN2 in CD8$^+$ T cells increased adhesion onto ICAM-1-positive cancer cells. FIG. 2a shows a schematic diagram of retroviral vector constructs containing TAGLN2 and eGFP or eGFP (EV) alone. Transduction efficiency of TAGLN2 or EV in OTI CD8$^+$ T cells was determined by flow cytometry FIG. 2b and western blotting FIG. 2c. FIG. 2d shows surface expression of ICAM-1 in B16F10 and E0771 cells. Cancer cells were stained with FITC-isotype control IgG or FITC-anti ICAM-1. The expression pattern of ICAM-1 was determined in both cell lines by flow cytometry and confocal microscopy. Data is representative of at least three independent experiments (b-d). *P<0.05. FIG. 2e shows representative flow cytometric profiles of conjugate formation between OTI CD8$^+$ T cells with/without TAGLN2 and B16F10 or E0771 cells in the absence or presence of OVA peptides. In some cases, control IgG or LFA-1-blocking antibodies were used. Shown on the right are the average percentages of conjugates. Data represents the means of three experiments±SDs. *P<0.05 versus OTI EV-CD8$^+$ T cells.

FIG. 3a OTI CD8$^+$ T cells with/without TAGLN2 were mixed with B16F10 or E0771 cells in the absence or presence of OVA peptides. mGZMB secretion in each condition was assessed by ELISA. Data is representative of at least three independent experiments. *P<0.05. FIG. 3b shows representative flow cytometric profiles for quantification of apoptotic cancer cells after incubation with OTI EV-CD8$^+$ T or OTI TG2-CD8$^+$ T cells. OTI EV-CD8$^+$ T or OTI TG2-CD8$^+$ T cells were mixed with PKH26-labeled cancer cells in the absence or presence of OVA peptides. After staining with 7-AAD, apoptotic cancer cells were determined by flow cytometry. Shown on the right are the average percentages of cytotoxicity. Data represents the means of three experiments. *P<0.05 versus OTI EV-CD8$^+$ T cells.

FIG. 4a-FIG. 4h shows that retroviral transduction of TAGLN2 potentiated the antitumor activity of CD8$^+$ T cells in vivo. FIG. 4a shows a schematic experimental design of T-cell adoptive transfer for determining the activity of OTI CD8$^+$ T cells. FIG. 4b shows infiltration of adoptively transferred OTI EV-CD8$^+$ T and OTI TG2-CD8$^+$ T cells into tumor sites. Confocal (top) and representative flow cytometric profiles (bottom, right) revealed tumor-infiltrated OTI EV-CD8$^+$ T and OTI TG2-CD8$^+$ T cells. The number of infiltrated cells per field (300 μm×300 μm) is represented as a bar graph (bottom, left). FIG. 4c and FIG. 4d show IHC and TUNEL analyses of OVA-E0771 tumors. IHC was performed using antibodies against mICAM-1, mCD8T, mKi-67, mIFN, and mGZMB. TUNEL assays were used to determine apoptotic cell death in tumor sites. Arrowheads indicate the TUNEL-positive cells. The average percentages of positive cells and TUNEL-positive cells were represented as bar graphs. *P<0.05. FIG. 4e shows schematic experimental design of T-cell immunotherapy for E0771 tumors. OTI EV-CD8$^+$ T or OTI TG2-CD8$^+$ T cells were intravenously injected into the tails of mice on days 7, 10, and 13 after tumor inoculation. Tumor weights and sizes are shown using a statistical weight graph FIG. 4f and photograph FIG. 4g. FIG. 4h shows a Kaplan-Meier survival curve of OVA-E0771 tumor-bearing mice after adoptive transfer of OTI EV-CD8$^+$ T or OTI TG2-CD8$^+$ T cells. Survival time was defined as the day of death or euthanasia due to a tumor greater than 3000 mm3 in size. *P<0.05 versus OTI EV-CD8+ T cells.

FIG. 5a-FIG. 5e shows that recombinant TAGLN2 fused with the protein transduction domain (TG2P) potentiated T-cell adhesion to APCs and cytokine release. FIG. 5a shows schematic diagram of TG2P and amino acid (a.a.) sequences consisting of the C-terminus of TAGLN2, linker a.a. sequences, and N-terminus of PTD. FIG. 5b shows transduction efficiency and stability of TG2P in CD3+ T cells. CD3+ T cells were incubated with the indicated concentrations of TG2P for 5 hours, and the cells were then subjected to western blot analysis FIG. 5c. The cells from FIG. 5b were cultured for the indicated times, and the retention time of TG2P in CD3+ T cells was analyzed. FIG. 5d shows conjugate formation. TG2P-CD3+ T cells were incubated with SEB-loaded B cells for 30 min, and the percentages of conjugates were determined by flow cytometry (left). The results are presented as bar graphs. In some cases, control IgG or anti-LFA-1 antibodies were used. Data is representative of at least three independent experiments (b-d). *P<0.05. FIG. 5e shows cytokine analysis. Secreted cytokines (mIL-2, mIFN and mGZMB) were measured by ELISA. mRNA levels were determined by qRT-PCR. Data represents the means of three experiments±SDs. *P<0.05 versus CD3+ T cells.

FIG. 6a shows conjugate formation. OTI non-CD8+ T or OTI TG2P-CD8+ T cells were incubated for 2 hours with E0771 cells in the absence or presence of OVA peptides, and the percentages of conjugates were then determined by flow cytometry (left). The results are presented as bar graphs (right). In some cases, control IgG or anti-LFA-1 antibodies were used. Data are representative of at least three independent experiments. *P<0.05. FIG. 6b shows cytotoxicity of TG2P-CD8+ T cells. The above cells in FIG. 6a were further incubated for 6 hours, and E0771 cell death (cytotoxicity) was then assessed by LDH release. FIG. 6c shows cytokine analysis. Secreted cytokines (mIL-2, mIFN, and mGZMB) were measured by ELISA. Data represents the means of three experiments±SDs. *P<0.05 versus OTI non-CD8+ T cells.

FIG. 7a-FIG. 7f shows that transduction of TG2P potentiated the antitumor activity of CD8+ cells in an E0771 tumor model. FIG. 7a shows infiltration of adoptively transferred OTI non-CD8+ T and OTI TG2P-CD8+ T cells into tumor sites. Confocal (top) and representative flow cytometric profiles (bottom, right) revealed tumor infiltrated OTI non-CD8+ T and OTI TG2P-CD8+ T cells. The numbers of infiltrated cells per field (300 μm×300 μm) are represented as a bar graph (bottom, left). FIG. 7b and FIG. 7c show IHC and TUNEL analyses of OVA-E0771 tumors. IHC was performed using antibodies against mICAM-1, mCD8T, mKi-67, mIFN, and mGZMB. TUNEL assays were used to determine apoptotic cell death in the tumor sites. The average percentages of positive cells and TUNEL-positive cells are represented as bar graphs. *P<0.05. Tumors were isolated; weights and sizes of tumors are presented as a weight graph FIG. 7d and photograph FIG. 7e. FIG. 7f shows Kaplan-Meier survival curves of OVA-E0771 tumor-bearing mice after adoptive transfer of OTI non-CD8+ T or OTI TG2P-CD8+ T cells. Survival time was defined as the day of death or euthanasia due to a tumor measuring more than 3000 mm3 in size. *P<0.05 versus OTI non-CD8+ T cells.

FIG. 8a shows conjugate formation. OTI Non-CD8+ T or OTI TG2P-CD8+ T cells were incubated for 2 hours with E0771 cells in the absence or presence of OVA peptides, and the percentages of conjugates were then determined by flow cytometry. Control IgG or anti-LFA-1 antibodies were used. FIG. 8b shows cytokine analysis. mRNA levels of cytokines (mIL-2, mIFN, and mGZMB) were determined by qRT-PCR. Data represents the means of three experiments±SDs. *P<0.05 versus OTI non-CD8+ T cells.

FIG. 9a shows conjugate formation. OTI non-CD8+ T or OTI TG2P-CD8+ T cells were incubated for 2 hours with B16F10 cells in the absence or presence of OVA peptides, and the percentages of conjugates were then determined by flow cytometry (left). The results are presented as bar graphs (right). Data are representative of at least three independent experiments. *P<0.05. FIG. 9b shows cytotoxicity of TG2P-CD8+ T cells. The above cells in FIG. 9a were further incubated for 24 hours, and B16F10 cell death (cytotoxicity) was then assessed by LDH release. FIG. 9c shows cytokine analysis. Secreted cytokines (mIL-2, mIFN, and mGZMB) were measured by ELISA. Data represents the means of three experiments±SDs. *P<0.05 versus OTI non-CD8+ T cells.

DETAILED DESCRIPTION

Mode for Invention

Figure 3A:
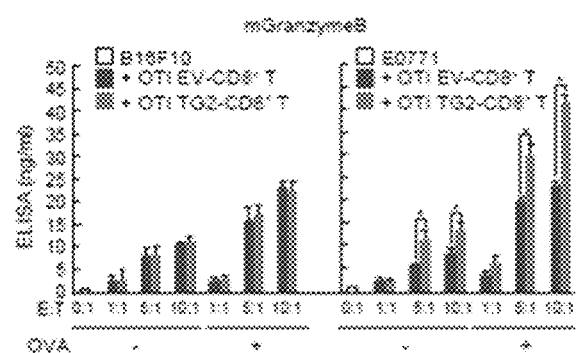
FIG. 3a and FIG. 3b shows that retroviral transduction of TAGLN2 potentiated cytokine release and enhanced the cytotoxic activity of OTI CD8$^+$ T cells against ICAM-1-positive cancer cells.

Hereinafter, the present disclosure will be described in more detail with reference to the following Examples. However, these Examples are for illustrative purposes only, and the invention is not intended to be limited by these Examples.

Experimental Example 1: Reagents and Antibodies

Rabbit polyclonal anti-TAGLN2 antibodies were raised in rabbits using purified full-length TAGLN2 (AbFrontier, Seoul, Korea). Rabbit polyclonal anti-green fluorescent protein (GFP) and rabbit polyclonal anti-β-actin antibodies were purchased from Santa Cruz Biotechnology (Santa Cruz, Calif., USA). Mouse polyclonal anti-His, anti-Vinculin, anti-Talin, anti-RapL, anti-LFA-1, anti-Rap1, horseradish peroxidase-conjugated anti-mouse IgG, and anti-rabbit or mouse IgG antibodies were obtained from Cell Signaling Technology (Danvers, Mass., USA). 145-2C11 (mouse anti-CD3; CRL-1975) and PV1 (mouse anti-CD28; HB-12352) hybridoma cell lines were purchased from the American Type Culture Collection (ATCC; Manassas, Va., USA). TS1/18 (anti-human LFA-1; HB-203) and R6.5 (anti-human ICAM-1) hybridoma cell lines were a gift from T. A. Springer (Harvard Medical School, Boston, Mass., USA). Anti-human CD28 and anti-mouse ICAM-1 antibodies were acquired from R&D Systems (Minneapolis, Minn., USA). Anti-mouse CD8a, anti-rabbit IFN, and anti-rabbit GZMB antibodies were obtained from Abcam (Cambridge, Mass., USA). Anti-mouse LFA-1, fluorescein isothiocyanate (FITC)-conjugated anti-mouse ICAM-1, and FITC-rat IgG1 isotype control antibodies were purchased from Biolegend (San Diego, Calif., USA). CellTracker CMFDA-green, CMRA-orange, and Lipofectamine reagent were obtained from Invitrogen (Carlsbad, Calif., USA). OVA peptide fragments (257-265) were purchased from InvivoGen (San Diego, Calif., USA). Staphylococcal enterotoxin E (SEE) and staphylococcal enterotoxin B (SEB) were obtained from Toxin Technology, Inc. (Sarasota, Fla., USA). Tetramethylrhodamine (TRITC)-phalloidin and poly-L-lysine (PLL) were purchased from Sigma (St. Louis, Mo., USA). PCR premix was purchased from Enzynomics (Daejeon, Korea). Restriction enzymes were purchased from New England Biolabs, Inc. (Beverly, Mass., USA). The plasmid DNA purification kit and WEST-ZOL Western Blot Detection kit were purchased from iNtRON Biotechnology (Seongnam, Korea). PrimeSTAR HS DNA polymerase was purchased from TaKaRa Bio Inc. (Shiga, Japan). Unless otherwise stated, all chemical reagents were purchased from Sigma.

Experimental Example 2: Cells

Jurkat T (TIB-152), E0771 (CRL-2755), and B16F10 (CRL-6475; all from ATCC) cells and Platinum-E (Plat-E) retroviral packaging cells (Cell Biolabs, San Diego, Calif., USA) were maintained in RPMI-1640 or Dulbecco's modified Eagle medium (Invitrogen) supplemented with 10% (v/v) fetal bovine serum (FBS; Invitrogen). Stable E0771 cells expressing OVA (pCL-neo-cOVA; Addgene, Cambridge, Mass., USA) were prepared by transfection with Lipofectamine 2000 reagent (Invitrogen) and selected with G418 (InvivoGen). Naive $CD3^+$ T cells were purified from mouse spleen and lymph nodes by negative selection using a T-cell enrichment column (R&D Systems). To generate mouse T-cell blasts, $CD3^+$ T cells were incubated in 2 μg/mL anti-CD3/28 coated culture plates with 100 U/mL rIL-2 for 48 hours and cultured for an additional 5 days with 100 U/mL rIL-2. Mouse splenocytes were dispersed and purified into $CD8^+$ and $CD19^+$ populations using EasySep (StemCell Technologies, Seattle, Wash., USA). The purity of each population was confirmed to be more than 95% by flow cytometry.

Experimental Example 3: cDNA Constructs

To generate TAGLN2, a TAGLN2 clone coding for the full-length open reading frame was purchased from ImaGene (Berlin, Germany). TAGLN2, TAGLN2ΔCR (Δ174-199), TAGLN2ΔCH (Δ2-136), and TAGLN2ΔAB (Δ153-160) genes were generated by standard or overlapping PCR, and subcloned into the pEGFP vector (Addgene).

To produce His-tagged TG2P, the pET-21a vector was used as an expression vector; this vector has a T7 promoter and provides six His residues at the C-terminus of the expressed protein. The coding sequence of TAGLN2 was amplified by PCR, and the products were incorporated into the pET-21a vector (Novagen, Madison, Wis., USA).

Experimental Example 4: Animals

C57BL/6 wild-type mice and OTI TCR transgenic mice (C57BL/6 background) were purchased from Jackson Laboratories (Bar Harbor, Me., USA). All mice were housed in specific pathogen-free conditions. All experimental methods and protocols were approved by the Institutional Animal Care and Use Committee of the School of Life Sciences, Gwangju Institute of Science and Technology and carried out in accordance with their approved guidelines.

Experimental Example 5: Retroviral Transduction from Mouse T Cell

Before retroviral transduction, mouse $CD3^+$ T cells from C57BL/6 mice or $CD8^+$ T cells from OTI TCR C57BL/6 mice were incubated in 2 μg/mL anti-CD3/28-coated plates with 100 U/mL hIL-2 for 48 hours. A total of $5 \times 10^6$ retroviral packaging cells (Plat-E; Cell Biolabs) were plated overnight in 10 $cm^2$ dishes. Retroviral particles were generated by transfection with retroviral vectors (empty vector, GFP, and TG2) and pCL-Eco packaging vector using Lipofectamine 2000 (Invitrogen). After 48 hours, virus supernatants (1 mL) were harvested, mixed with $10^6$ mouse T cells, incubated in 12-well plates coated with 20 μg/mL retronectin, and centrifuged for 90 minutes at 2,000×g at 25° C. with 100 U/mL hIL-2. The transduced T cells were maintained with fresh media with hIL-2 and expanded for 5 to 8 days.

Experimental Example 6: Determination of Cellular F-Actin Contents

Cells were maintained in serum-free medium for 12 hours and incubated with anti-CD3/28 for the indicated times at 37° C. The reactions were terminated by adding 4% paraformaldehyde. Fixed cells were washed once with PBS and resuspended in PBS containing 1% bovine serum albumin and 0.25% Triton X-100 for 5 minutes. After permeabilization, the cells were washed, stained for 30 minutes with TRITC-phalloidin (Sigma), and then analyzed by flow cytometry.

Experimental Example 7: Analysis of Adhesion

T cells and target cells (B cell, B16F10, and E0771) were stained with Cell Tracker Green CMFDA and Orange CMRA, respectively, in accordance with the manufacturer's protocols (Invitrogen). B cells ($5 \times 10^5$) were incubated with 5 μg/mL SEB or vehicle control for 30 minutes, washed, and resuspended in RPMI 1650 medium. E0771 or B16F10 cells ($5 \times 10^5$) were incubated with 10 μg/mL OVA257-264 peptides for 30 minutes, washed, and resuspended in RPMI 1640 medium.

For conjugation, equal volumes of the T cells and target cells were mixed and incubated at 37° C. The relative proportion of green, orange, and green-orange events in each tube was determined by two-color flow cytometry using FACSCanto (BD Biosciences, San Jose, Calif., USA), and analyzed with FlowJo software (Treestar, San Carlos, Calif., USA). The number of gated events counted per sample was at least 10,000. The percentage of the conjugated T cells was determined as the number of dual-labeled (CMFDA- and CMRA-positive) events divided by the number of CMFDA-positive T cells.

Experimental Example 8: Observation with Confocal Microscopy

To investigate TAGLN2 localization, Jurkat T cells expressing TG2 GFP were transfected with LifeA_RFP, and incubated for 30 minutes with 1 μg/mL SEE-pulsed Raji B cells stained with ICAM-1_Cy5. The cells were then placed on PLL-coated glass and imaged using a 100×, NA 1.40 oil immersion objective on a laser-scanning confocal microscope (FV1000; Olympus, Tokyo, Japan).

To evaluate ICAM-1 expression in B16F10 and E0771 cells, cells were detached using 10 mM ethylenediaminetetraacetic acid, stained with anti-ICAM-1-FITC, and observed using a 60×, NA 1.40 oil immersion objective. In some conjugation assays, samples were prepared as described above, and E0771 ($5 \times 10^5$) cells were stained with CMRA-orange cell tracker for 30 minutes, washed, and seeded on glass-bottom confocal dishes for 24 hours. The next day, EV- or TG2P-treated OTI $CD8^+$ T cells ($5 \times 10^5$) were stained with CMFDA-green and incubated with cancer cells for 2 hours. The unattached cells were removed by washing with warm PBS and observed using a 40×, NA 1.40 oil immersion objective.

Experimental Example 9: Western Blotting

Cells were lysed in an ice-cold lysis buffer (50 mM Tris-HCl, pH 7.4, containing 150 mM NaCl, 1% Triton X-100, and a protease inhibitor) for 15 minutes on ice. Cell lysates were centrifuged at 16,000×g for 30 minutes at 4° C., and the supernatants were eluted with an SDS sample buffer (100 mM Tris-HCl, pH 6.8, 4% SDS, and 20% glycerol with bromophenol blue) and heated for 5 minutes. The proteins were separated by SDS PAGE on 10% to 15% gels and were transferred to nitrocellulose membranes using a Trans-Blot SD semidry transfer cell (Bio-Rad, Hercules, Calif., USA).

The membrane was blocked in 5% skim milk (1 hour), rinsed, and incubated with appropriate antibodies in TBS containing 0.1% Tween 20 (TBS-T) and 0.5% skim milk overnight. Excess primary antibody was then removed by washing the membrane three times in TBST. The membrane was then incubated with 0.1 µg/mL peroxidase-conjugated secondary antibodies (anti-rabbit or anti-mouse) for 1 hour. After three washes with TBST, bands were visualized using western blotting detection reagents and were then exposed to X-ray film (Kodak, Rochester, N.Y., USA).

Experimental Example 10: Immunoprecipitation (IP)

Cell lysates were pre-cleared, and the supernatants were incubated with the antibodies overnight at 4° C., followed by incubation with protein A/G agarose beads (Santa Cruz Biotechnology). The beads were collected and washed with PBS, and then resuspended with a 5× SDS loading buffer. The immunoprecipitated proteins were separated by SDS-PAGE on 12% gels, and analyzed by Western blotting, as described above.

Experimental Example 11: Pull-Down Analysis for Rap1

Active GTP-bound Rap1 levels were measured using an EZ-Detect Rho activation kit in accordance with the manufacturer's instructions (Thermo Fisher Scientific Inc., Rockford, Ill., USA). Specifically, Jurkat T cells expressing GFP or TG2_GFP cells were stimulated with anti-CD3/28 at 37° C. for an indicated times, washed once with ice-cold PBS, and lysed in a buffer containing 20 mM Tris-HCl, pH 7.4, 150 mM NaCl, 1% Triton X-100, and protease inhibitor cocktail.

The samples were incubated on ice for 20 minutes, followed by centrifugation (16,000×g, 30 minutes, 4° C.). Equal amounts of supernatants were incubated with GST-RalGDS-RBD/GSH-beads for GTP-Rap1 for 12 hours at 4° C. The beads were washed three times with the lysis buffer, and the bound proteins were eluted with sample buffer by boiling. Samples were electrophoresed and analyzed by Western Blotting with anti-Rap1 antibodies.

Experimental Example 12: Flow Cytometric Analysis

The cells were suspended in PBS containing 2% FBS, and stained with fluorescent-conjugated antibodies against mouse ICAM-1 or isotype control for 15 minutes at room temperature. The cells were then assessed on a FACSCanto (BD Biosciences), and the resulted data were analyzed with FlowJo software (Treestar).

Experimental Example 13: Measurement of Cytokine Secretion $CD3^+$ T or OTI $CD8^+$ T cells were stimulated with SEB-loaded B cells or OVA-loaded cancer cells. After incubation for the indicated times, the amounts of mIL-2, mIFNγ, and mGZMB in a supernatant were measured by ELISA.

Experimental Example 14: In Vitro Cytotoxicity Assay

For in vitro cytotoxic T-cell activity assays, OTI $CD8^+$ T cells were generated and incubated with E0771 or B16F10 cells in the absence or presence of OVA. After 6 hours or 24 hours, cell-mediated cytotoxicity was determined using a Pierce LDH Cytotoxicity Assay Kit (Thermo Scientific Inc.), and the percent cytotoxicity was calculated according to the manufacturer's instructions.

For flow cytometric cytotoxicity assays, PKH26 (Sigma) was diluted according to the manufacturer's kit directions. E0771 or B16F10 cells were washed in PBS and resuspended in 1 mL diluent C from the kit. The PKH26 was diluted to 4 µM in 1 mL diluent C. Cells were combined with dye, and the tube was inverted several times over 3 minutes. About 2 mL FBS was added to the tube, and tube was inverted continuously for 1 minute. Cells were then transferred to 15 mL conical tubes with 4 mL phenol red-free of RPMI 1640 with 10% FBS and washed three times in the same medium. OTI $CD8^+$ T cells were washed twice in phenol red-free RPMI with 10% FBS, mixed with PKH26-labeled cancer cells, and incubated at 37° C. for 4 hours. After incubation, 10 µL of a 5 µg/mL solution of 7-AAD was added to the cell suspension for 10 minutes on ice. Cells were evaluated on a FACSCanto (BD Biosciences), and data were analyzed with FlowJo software (Treestar).

Experimental Example 15: Xenograft Model

For the preparation of an OVA-E0771 tumor model, the fourth mammary fat pads of 8-week-old C57BL/6 female mice were orthotopically injected with $5 \times 10^5$ OVA-E0771 cells on day 0. The mice were conditioned with 5 Gy total body irradiation immediately before T cell transfer. OTI $CD8^+$ T ($1 \times 10^7$ cells), OTI TG2-$CD8^+$ T, or OTI TG2P-$CD8^+$ T cells were injected into the tail vein on days 7, 10, and 13 after tumor inoculation. The animals were sacrificed 28 days after tumor injection, and tumors were weighed and imaged.

For analysis of the in vivo activity of TG2-loaded $CD8^+$ T cells, OTI $CD8^+$ T ($1 \times 10^7$ cells), OTI TG2-$CD8^+$ T, or OTI TG2P-$CD8^+$ T cells were injected into the tail vein on day 14 after tumor inoculation. Two days later, animals were sacrificed, and tumor tissues were extracted.

For immunofluorescence, tumor tissues were fixed in 4% paraformaldehyde for 2 hours at room temperature, washed with PBS, and dehydrated in 30% sucrose until tumor tissues sunk. Tissues were then cryoprotected with Tissue-Tek OCT (Sakura Finetek, Torrance, Calif., USA), and 10 µm cryo-sections were mounted with Fluorescent Mounting Medium (Dako, Carpinteria, Calif., USA). Images were obtained using a 40×, NA 1.40 oil immersion objective on a laser-scanning confocal microscope (FV1000).

To compare the amounts of tumor infiltrated $CD8^+$ T cells (OTI $CD8^+$ T (green) and OTI TG2-$CD8^+$ T (green/red) or OTI TG2P-$CD8^+$ T (red) cells, tumor tissues were homogenized in PBS, and cells were evaluated on a FACSCanto (BD Biosciences). Data was analyzed with FlowJo software (Treestar).

For immunohistochemistry, the extracted tumor tissues were fixed in 4% paraformaldehyde and embedded in paraffin. Tissue slices (5 µm) were incubated with anti-ICAM-1, anti-CD8T, anti-Ki67, anti-GZMB, and anti-INF antibodies or TdT-BiOTIn-dUTP mix (100 µL TdT buffer [30 mM Tris, pH 7.2, 140 mM sodium cacodylate, 1 mM cobalt chloride], 30 U TdT, and 0.5 µL BiOTIn-dUTP mix [Boehringer Mannheim, Indianapolis, Ind., USA]) followed by diamino-benzidine staining (Dako and R&D Systems) according to the manufacturer's instructions. TUNEL assays were performed using an In Situ Cell Death Detection kit, AP (Roche, Mannheim, Germany). Microscopy images were analyzed using ImmunoRatio (http://imtmicroscope.uta.fi/immunoratio) or recorded by a pathologist.

Experimental Example 16: Purification of TG2P

Expression of TG2P in *Escherichia coli* BL21 (DE3) cells was performed as described for transduction of the aforementioned recombinant plasmids. The expression of TG2P was induced by addition of 0.5 mM isopropyl β-D-1-thiogalactopyranoside to the culture medium overnight at 25° C., and cells were then collected. The cell pellets were resuspended in PBS, sonicated, and centrifuged. After centrifugation, the TG2P in the supernatant was purified by affinity chromatography on a His-selected Nickel Affinity gel (Sigma). The gel was equilibrated with 10 volumes of buffer (50 mM sodium phosphate, pH 8.0, and 0.3 M NaCl) and incubated with the supernatant. The gel was washed with 5 volumes of wash buffer (50 mM sodium phosphate, pH 8.0, 0.3 M NaCl, and 10 mM imidazole). The TG2P was eluted with increasing concentrations of imidazole up to 250 mM. The eluted TG2P was desalted using PD-10 Sephadex G-25 (Amersham Pharmacia Biotech, Uppsala, Sweden), supplemented with 10% glycerol and separated into aliquots, followed by flash-freezing at −70° C.

Experimental Example 17: Reverse Transcription PCR (RT-PCR) and Real-Time Quantitative RT-PCR (qRT-PCR)

Total RNA was isolated from cells using TRIzol reagent (Molecular Research Center, Cincinnati, Ohio, USA). cDNA was prepared using RT Premix. Real-time qPCR was conducted in an ABI PRISM 7300 RT-PCR system using a SYBRreen PCR Master Mix (Applied Biosystems, Carlsbad, Calif., USA). Gene-specific primers (forward and reverse primer pairs, respectively) are shown in Table 1 below.

TABLE 1

| Gene | Primer 5'→3' (Forward) | SEQ ID NO | Primer 5'→3' (Reverse) | SEQ ID NO |
|---|---|---|---|---|
| IL-2 | CACGTCTTGCACTTGTCAC | 3 | CCTTCTTGGGCATGTAAAACT | 4 |
| INFγ | GCTCTGAGACAATGAACGCT | 5 | AAAGAGATAATCTGGCTCTG | 6 |
| GZMB | TTTCATCCTGTAATTGGACTAA | 7 | GCGATCTCCACACTTCTC | 8 |
| GAPDH | GCACAGTCAAGGCCGAGAAT | 9 | GCCTTCTCCATGGTGGTGAA | 10 |

The mRNA levels of the target genes relative to GAPDH were normalized using the following formula: relative mRNA expression=$2-(^{\Delta Ct\ of\ target\ gene-\Delta C\ of\ GAPDH})$, where Ct is the threshold cycle value. In each sample, the expression of the analyzed gene was normalized to that of GAPDH, and described as the mRNA level relative to GAPDH.

Experimental Example 18: Statistical Analysis

Mean values were calculated using data taken from at least three independent experiments conducted on different days. In the case of the significance testing, unpaired Student's t tests and one-way analysis of variance tests were used. Differences between groups were considered significant when the P value was less than 0.05.

Example 1: Determination Whether TAGLN2, an F-Actin Stabilizer, is a Cytoplasmic Factor Modulating "Inside-Out" Signal of LFA-1

TAGLN2 (TG2), predominantly expressed in lymphocytes, is highly concentrated at the peripheral actin ring of an IS (FIG. 1a), and corresponds to increased F-actin contents (FIG. 1b) and T-APC conjugate formation (FIG. 1c) (Na, B.-R. et al. The Journal of Cell Biology 209, 143-162 (2015)). It was found in the present disclosure that regardless of stimulation, TAGLN2 was physically associated with LFA-1 through its CH domain (FIGS. 1d and 1e) and corresponded to the activation of Rap1 (FIG. 1f), which functions as a key regulator of LFA-1-dependent adhesion and migration of T cells.

These results suggested that TAGLN2, in addition to its biochemical characteristics enabling it to control actin dynamics, acted as a cytosolic factor to modulate "inside-out" signaling of the integrin LFA-1.

FIG. 1g indicates the potential mechanisms of action of TAGLN2 in T cells. TAGLN2 was confirmed to not only stabilize F-actin but also block cofilin-mediated actin polymerization, resulting in increased F-actin contents at the IS and leading to prolonged T cell activation and IL-2 production. In addition, TAGLN2 was found to regulate "inside-out" integrin LFA-1 function when T cells received a primary antigen signal through the TCR even though the "outside-in" costimulatory signals were weak in the tumor microenvironment. This led to the stable adhesion of T cells onto the tumor target cells (FIG. 1g).

These dual regulatory mechanisms of TAGLN2 enhanced T cell activation, thereby leading to a hypothesis that TAGLN2 could be a potential effector molecule capable of potentiating cancer cell killing via cell therapies. That is, TAGLN2 may be applicable in many types of cancer immunotherapy including CAR or TCR transgene-adopted cytotoxic T and NK cells.

Example 2: Adhesion of Cytotoxic T Cells onto Cancer Cells

In order to determine whether the retroviral transduction of TAGLN2 potentiates the adhesion of cytotoxic T cells onto ICAM-1-positive cancer cells, a retroviral DNA construct containing wild-type TAGLN2 and eGFP genes or eGFP (empty vector [EV]) alone was generated (FIG. 2a).

Specifically, retroviral particles containing TAGLN2 or EV were produced from host plat E cells and infected into mouse primary CD8$^+$ T cells for determination of the viral transduction efficiency by flow cytometry. The efficiency was generally over 80% (FIG. 2b), and was also confirmed by Western blotting (FIG. 2c).

As the conjugation of T cells with APCs was observed, the expression levels of ICAM-1 in two cancer cell lines were observed to find whether TAGLN2 expression may influence CD8$^+$ T cell adhesion to cancer cells via the LFA-1/ICAM-1 interaction.

As a result, B16F10 melanoma expressed little ICAM-1, whereas E0771 breast cancer cells expressed relatively high amounts of ICAM-1 (FIG. 2d).

Further, during the conjugation assays, the OTI TCR+ CD8$^+$ T cells overexpressing TG2 (OTI TG2-CD8$^+$ T cells) showed significant increases in the numbers of the conjugates when incubated with OVA257-264 peptide-loaded cells (OVA257-264), but not with the OVA-loaded B16F10 (OVA-B16F10) (FIG. 2e). This conclusion was further corroborated by anti-LFA-1 antibodies, but not the control IgG, which significantly reduced the number of conjugates between TG2-CD8$^+$ T cells and E0771 cells (FIG. 2e). This suggests that the costimulatory LFA-1/ICAM-1 interaction was critical for cytotoxic T-cell adhesion to ICAM-1$^+$ cancer target cells.

Example 3: Cytokine Release and Cytotoxicity

Whether the strong conjugation of OTI TG2-CD8$^+$ T cells with E0771 cells was correlated with increased cytokine release cytotoxicity was measured.

Figure 3B:
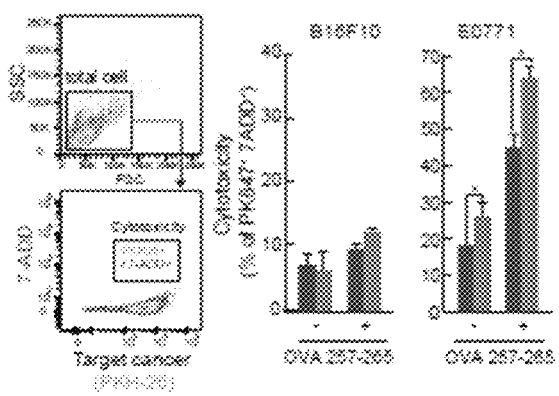

Specifically, mGranzyme B (mGZMB) was observed to be significantly elevated in the population of OTI TG2-CD8$^+$ T cells interacting with OVA-E0771 cells (FIG. 3a). These cells significantly lysed E0771 cells, but not B16F10 cells (FIG. 3b).

This suggests that overexpression of TG2 influenced the ability of OTI CD8$^+$ T cells to effectively kill tumor cells, presumably by upregulating actin-dependent signaling pathways and promoting costimulatory LFA-1 activation.

Example 4: Potentiation of Anti-Tumor Activity

As it was revealed in vitro in Example 3 that the OTI TG2-CD8$^+$ T cells showed increased conjugation with target cancer cells together with enhanced cytokine release and higher cytotoxicity, the effectiveness of OTI TG2-CD8$^+$ T cells was to be examined in vivo.

To this end, OVA-E0771 cells were implanted into the mammary fat pads of C57BL/6 female mice. 14 days later, the mice were injected intravenously with OTI EV-CD8$^+$ T and/or OTI TG2-CD8$^+$ T cells (FIG. 4a). 2 days later, the mice were sacrificed, and cancerous tissues were removed. Cryosection of the removed cancer tissues showed that both EV-CD8$^+$ T and TG2-CD8$^+$ T cells were similarly targeted to tumors originating from E0771 cells, as determined by confocal and FACS analyses (FIG. 4b).

Immunohistochemistry was used to determine the expression levels of several proteins and the number of apoptotic cells in the tumor sites, and found that cells positive for mKi67, a cancer cell proliferation marker, were decreased, whereas cells positive for interferon gamma (mIFNγ), mGZMB, and terminal deoxynucleotidyl transferase dUTP nick end labeling (TUNEL) staining were significantly increased in the tumor sites injected with the OTI TG2-CD8$^+$ T cells compared with OTI EV-CD8$^+$ T cells (FIGS. 4c and 4d).

To evaluate the effects of OTI TG2-CD8$^+$ T cells on tumor growth in vivo, OVA-E0771 cells were implanted into the mammary fat pads of C57BL/6 mice. Seven days later, the mice were randomized into three groups for administration of OTI CD8$^+$ T cells. OTI EV-CD8$^+$ T or OTI TG2-CD8$^+$ T cells were injected intravenously three times at 3-day intervals (FIG. 4e). All animals were sacrificed 28 days after tumor injection, and the tumors were weighed.

As a result, the average tumor weight from mice injected with OTI EV-CD8$^+$ T cells was lower than that of tumors without cell injection, suggesting that adoptive cytotoxic T cell transfer efficiently reduced tumor growth in vivo.

Further, intravenous administration of OTI TG2-CD8$^+$ T cells significantly reduced tumor size compared with that of tumors without adoptive cell transfer or tumors transferred with OTI EV-CD8$^+$ T cells (FIGS. 4f and 4g). Kaplan-Meier survival studies 28 days after the tumor injection showed that untreated mice and mice receiving non-transduced T cells had median survival times of 20 days and 27 days, respectively. In contrast, the mice injected with OTI TG2-CD8$^+$ T cells had a 75% probability of surviving longer than 28 days (FIG. 4h).

Example 5: T Cell Adhesion and Cytokine Release of Recombinant TAGLN2

Whether the recombinant TAGLN2 fused with PTD (TG2P) was efficiently internalized into T cells and enhances T-cell adhesion and cytokine release was measured.

Small protein domains, commonly referred to as PTDs, are used to deliver certain therapeutic macromolecules into eukaryotic cells. To overcome the disadvantages of virus-mediated gene delivery systems, such as inconsistent transduction efficiency, long-term preparation, high cost, and safety issues, a TAGLN recombinant protein fused with PTD (TG2P), which was easier and faster to transduce into mouse primary T cells, was prepared (FIG. 5a). TG2P (0 μM to 10 μM) was readily internalized into the T cells, and the internalized TG2P was as stable as endogenous TAGLN2 for at least 24 hours (FIGS. 5b and 5c).

Next, whether treatment with TG2P showed the same efficacy as viral transduction of TAGLN2 in terms of CD3$^+$ T cell adhesion to antigen-loaded B cells was to be determined.

It was found that CD3$^+$ T cells treated with TG2P (TG2P-CD3$^+$ T cells) significantly increased the number of conjugates when cells were incubated with SEB-loaded B cells TG2P. The number of conjugates was correlated with the concentration of TG2P used to treat T cells (FIG. 5d). In accordance with the results of viral gene delivery, significant upregulation of mIL-2, mIFNγ, and mGZMB was observed in the population of TG2P-CD3$^+$ T cells incubated with SEB-loaded B cells (FIG. 5e). These results indicated that PTD-based transduction was as effective as retrovirus-based gene delivery in CD3$^+$ T cells.

Figure 6A:
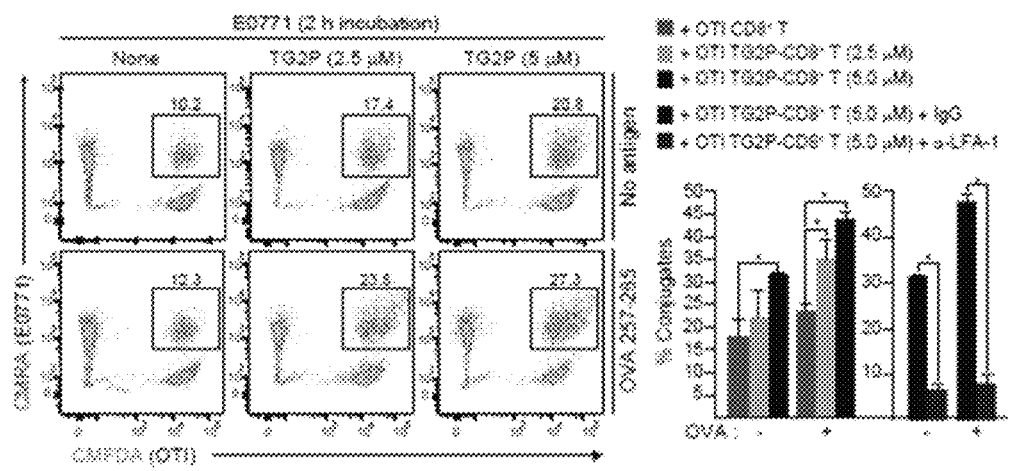
FIG. 6a-FIG. 6c shows that transduction of TG2P in CD8+ T cells increases adhesion and cytokine release in response to ICAM-1-positive cancer cells.
Figure 8A:
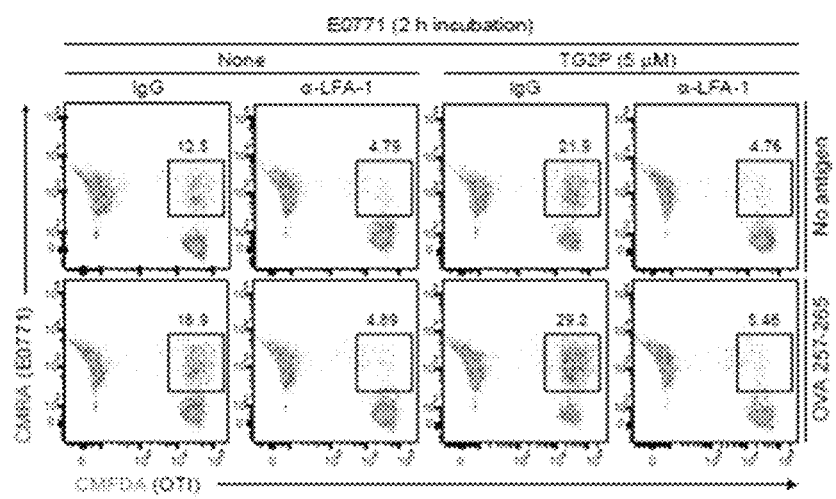
FIG. 8a and FIG. 8b shows that transduction of TG2P in CD8+ T cells increased adhesion onto E0771 cells and enhanced cytokine production.

Based on the results above, TG2P was applied to the OTI CD8$^+$ T cells to establish OTI TG2P-CD8$^+$ T cells. Treatment with TG2P significantly increased the number of OTI CD8$^+$ T-OVA-E0771 conjugates (FIGS. 6a and 8a). In addition, strong inhibition of adhesion by antibodies targeting LFA-1 demonstrated that the effect of TG2P was mediated through activation of LFA-1.

Figure 6B:
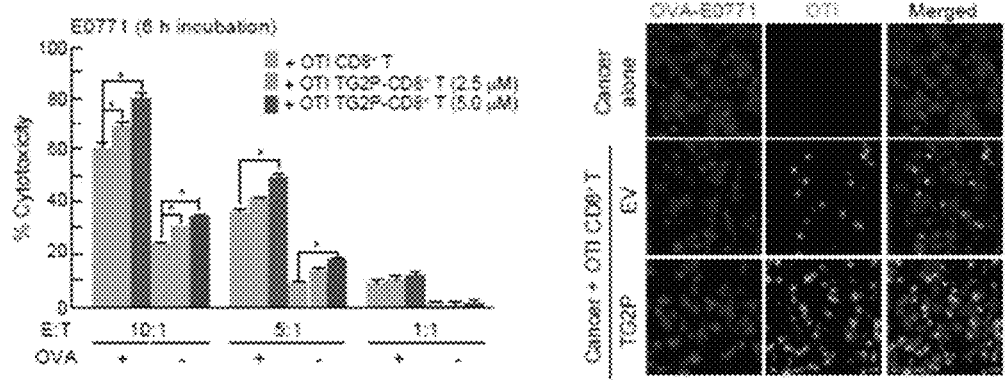
Figure 6C:
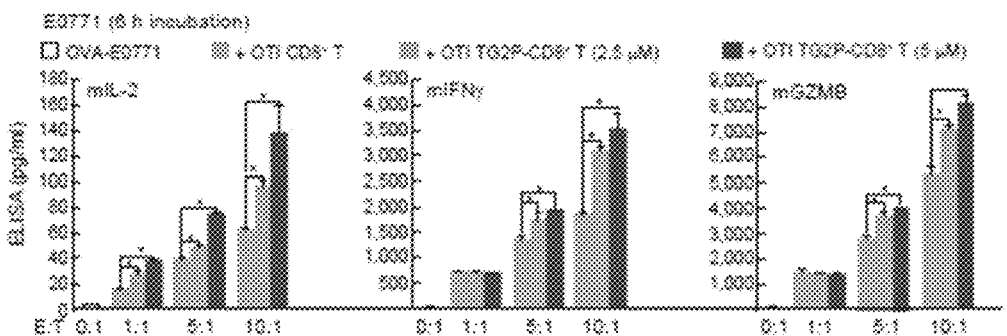
Figure 8B:
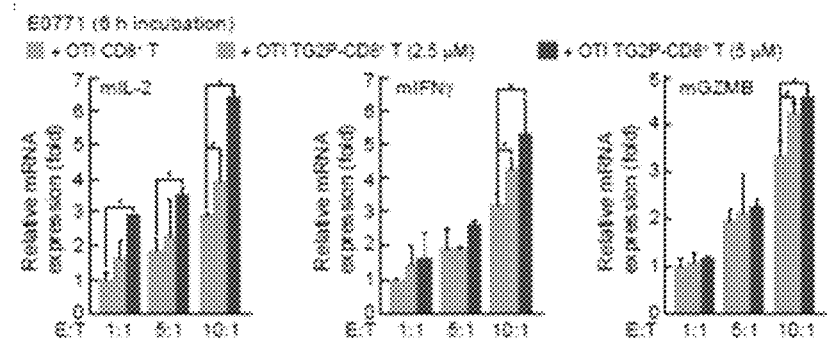
Figure 9A:
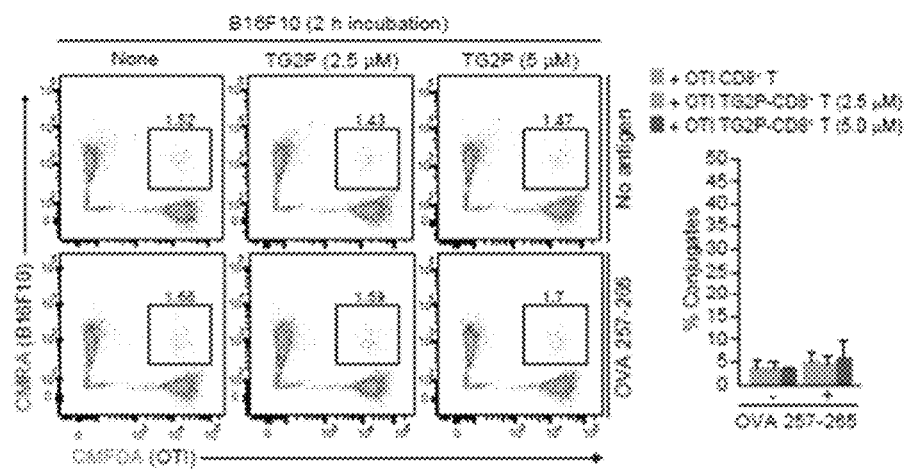
FIG. 9a-FIG. 9c shows that transduction of TG2P in CD8+ T cells did not increase adhesion to B16F10 cells and showed no significant effects on cytokine release or cytotoxic activity.
Figure 9B:
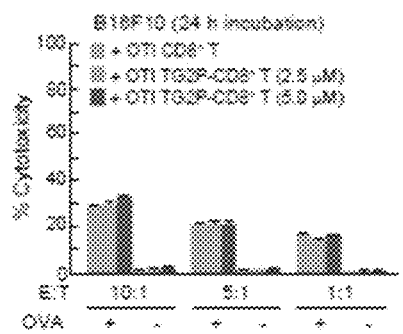
Figure 9C:
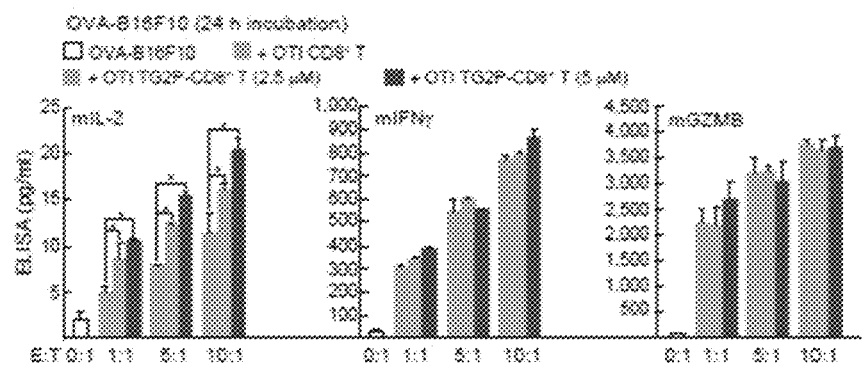

OTI TG2P-CD8$^+$ T cells also produced more cytokines, such as mIL2, mIFNγ, and mGZMB (FIGS. 6c and 8b), and exerted strong cytotoxic activity against E0771 cells (FIG. 6b). In contrast, OTI TG2P-CD8$^+$ T cells did not affect ICAM-1$^-$ OVA-B16F10 cells (FIG. 9), suggesting that the adhesive interaction between cytotoxic T cells and cancer cells through LFA-1/ICAM-1 was critical.

Example 6: Anti-Tumor Activity of Recombinant TAGLN2 (TG2P)

As shown in FIG. 4a, whether the CD8$^+$ T cells would move toward a tumor in the presence or absence of TG2P after the tumor was introduced was measured.

Cryosection of removed cancer tissues shows that both CD8$^+$ T cells were similarly targeted into the E0771 cells. Further, the expression levels of several proteins and the number of apoptotic cells were measured in the tumor sites, and as a result, it was found that all results were similar to those obtained from OTI TCR TG2-CD8$^+$ T cells (FIGS. 7b, 7c, 4c, and 4d).

The effects of OTI TG2P-CD8$^+$ T cells on tumor growth in vivo was further to be evaluated.

It was found that OTI TG2P-CD8$^+$ T cells significantly reduced the average tumor weight compared with that of tumors without adoptive cell transfer or treated with OTI CD8$^+$ T cells without TG2P, suggesting that recombinant TG2P had effects similar to those of retrovirus-based gene delivery (FIGS. 7d and 7e).

Kaplan-Meier survival studies showed that untreated mice and mice treated with non-transduced OTI T cells had a median survival of 21 and 23 days, respectively. In contrast, mice adoptively transferred with OTI TG2P-CD8$^+$ T cells had a 70% or higher probability of surviving more than 28 days (FIG. 7f).

Such results suggest that due to the high adhesion activity of the present disclosure to tumor cells, the recombinant TG2P effectively decreases tumor cell growth and increases survivability.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A recombinant protein for treating cancer consisting of an amino acid sequence of SEQ ID NO: 1, which is loaded in a cancer killer cell to improve cytotoxic activity of the cancer killer cell, the cancer killer cell being a tumor-infiltrated T lymphocyte, T cell, or a natural killer cell including a chimeric antigen receptor, wherein the recombinant protein is further fused with a protein transduction domain (PTD) consisting of an amino acid sequence of SEQ ID NO: 2.

2. The recombinant protein of claim 1, wherein the fusion of PTD is by a peptide linker or direct fusion.

3. The recombinant protein of claim 1, capable of stabilizing actin polymerized in an immunological synapse by stimulation of a T-cell antigen receptor.

4. The recombinant protein of claim 1, wherein cytokine expression is increased when the recombinant protein is loaded in the cancer killer cell compared to a control group in which the recombinant protein is not loaded in the cancer killer cell.

5. The recombinant protein of claim 4, wherein the cytokine is at least one of mIL-2, mIFNγ, and mGZMB.

6. A recombinant protein-loaded cancer killer cell, wherein the cancer killer cell comprises the recombinant protein of claim 1, the cancer killer cell being a tumor-infiltrated T lymphocyte, T cell, or a natural killer cell including a chimeric antigen receptor, wherein the recombinant protein is further fused with a protein transduction domain (PTD) consisting of an amino acid sequence of SEQ ID NO: 2.

7. The recombinant protein-loaded cancer killer cell of claim 6, wherein the loading of the recombinant protein in the cancer killer cell is performed by:
   i) transduction of a polynucleotide encoding the recombinant protein consisting of the amino acid sequence of SEQ ID NO:1 by retrovirus, wherein the recombinant protein is further fused with a protein transduction domain (PTD) consisting of an amino acid sequence of SEQ ID NO: 2.

8. A pharmaceutical composition for treating cancer, comprising:
   i) a recombinant protein for treating cancer consisting of an amino acid sequence of SEQ ID NO: 1, which is loaded in a cancer killer cell to improve cytotoxic activity of the cancer killer cell; wherein the recombinant protein is further fused with a protein transduction domain (PTD) consisting of an amino acid sequence of SEQ ID NO: 2, wherein the cancer killer cell comprises the recombinant protein, the cancer killer cell being a tumor-infiltrated T lymphocyte, T cell, or a natural killer cell including a chimeric antigen receptor.

9. The pharmaceutical composition for treating cancer of claim 8, wherein the cancer is lung cancer, gastric cancer, colon cancer, breast cancer, bone cancer, pancreatic cancer, skin cancer, head cancer, head and neck cancer, melanoma, uterine cancer, ovarian cancer, colon cancer, small intestine cancer, rectal cancer, anal cancer, fallopian tube cancer, endometrial cancer, cervical cancer, vaginal cancer, vulva cancer, Hodgkin's disease, esophageal cancer, lymph node cancer, bladder cancer, gall bladder cancer, endocrine cancer, prostate cancer, adrenal gland cancer, soft tissue sarcoma, urethral cancer, penile cancer, chronic or acute leukemia, lymphocytic lymphoma, renal cancer, ureteral cancer, renal pelvic cancer, central nervous system (CNS) tumor, spinal cord tumor, brainstem glioma, or pituitary adenoma.

10. A method for producing a recombinant protein-loaded cancer killer cell, comprising:
   (a) fusing a PTD consisting of an amino acid sequence of SEQ ID NO: 2 into an amino acid of SEQ ID NO: 1; and
   (b) introducing the fusion protein of (a) into a cancer killer cell, the cancer killer cell being a tumor-infiltrated T lymphocyte, T cell, or a natural killer cell including a chimeric antigen receptor.

11. A method for producing a recombinant protein-loaded cancer killer cell, comprising: transducing into a cancer killer cell using retrovirus comprising a polynucleotide encoding an amino acid sequence of SEQ ID NO: 1, fused with a protein transduction domain (PTD) consisting of an amino acid sequence of SEQ ID NO: 2, the cancer killer cell being a tumor-infiltrated T lymphocyte, T cell, or a natural killer cell including a chimeric antigen receptor.

12. The recombinant protein-loaded cancer killer cell of claim 6, wherein the loading of the recombinant protein in the cancer killer cell is performed by:
   i) transduction of a polynucleotide encoding the recombinant protein consisting of the amino acid sequence of SEQ ID NO: 1 further fused with a protein transduction domain (PTD) consisting of an amino acid sequence of SEQ ID NO: 2 by retrovirus.

13. The recombinant protein-loaded cancer killer cell of claim 6, wherein the loading of the recombinant protein in the cancer killer cell is performed by:
   i) introduction in the form of the recombinant protein consisting of sequence of SEQ ID NO: 1 further fused with a protein transduction domain (PTD) consisting of an amino acid sequence of SEQ ID NO: 2.

* * * * *